(12) United States Patent
Kwon et al.

(10) Patent No.: US 9,920,351 B2
(45) Date of Patent: *Mar. 20, 2018

(54) RAPID ANTIBIOTIC SUSCEPTIBILITY TESTING SYSTEM BASED ON BACTERIAL IMMOBILIZATION USING GELLING AGENT, ANTIBIOTIC DIFFUSION AND TRACKING OF SINGLE BACTERIAL CELLS

(71) Applicants: SNU R & DB FOUNDATION, Seoul (KR); QUANTAMATRIX, Seoul (KR)

(72) Inventors: Sunghoon Kwon, Seoul (KR); Yong-Gyun Jung, Seoul (KR); Jung Il Choi, Seoul (KR); Hun Jong Na, Seoul (KR)

(73) Assignee: QUANTAMATRIX INC., Seoul (KR)

( * ) Notice: Subject to any disclaimer, the term of this patent is extended or adjusted under 35 U.S.C. 154(b) by 115 days.

This patent is subject to a terminal disclaimer.

(21) Appl. No.: 14/793,740

(22) Filed: Jul. 8, 2015

(65) Prior Publication Data

US 2015/0315625 A1 Nov. 5, 2015

Related U.S. Application Data

(63) Continuation of application No. 13/756,872, filed on Feb. 1, 2013, now Pat. No. 9,133,498.

(60) Provisional application No. 61/593,407, filed on Feb. 1, 2012.

(30) Foreign Application Priority Data

Feb. 2, 2012 (KR) .................. 10-2012-0011002

(51) Int. Cl.
| | |
|---|---|
| *C12Q 1/18* | (2006.01) |
| *C12N 11/04* | (2006.01) |
| *B29C 45/00* | (2006.01) |
| *B29L 31/00* | (2006.01) |

(52) U.S. Cl.
CPC ............ *C12Q 1/18* (2013.01); *B29C 45/0001* (2013.01); *C12N 11/04* (2013.01); *B29L 2031/752* (2013.01)

(58) Field of Classification Search
CPC ........................................................ C12Q 1/18
See application file for complete search history.

(56) References Cited

U.S. PATENT DOCUMENTS

| | | | | |
|---|---|---|---|---|
| 6,416,969 B2 * | 7/2002 | Matsumura | ............. | C12Q 1/04 435/283.1 |
| 7,341,841 B2 | 3/2008 | Metzger | | |
| 7,687,239 B2 | 3/2010 | Goldberg et al. | | |
| 8,071,319 B2 | 12/2011 | Metzger et al. | | |
| 8,460,887 B2 | 6/2013 | Goldberg et al. | | |
| 8,895,255 B1 | 11/2014 | Goldberg et al. | | |
| 9,133,498 B2 * | 9/2015 | Kwon | ............. | C12Q 1/18 |
| 2013/0217063 A1 | 8/2013 | Metzger et al. | | |
| 2014/0038171 A1 | 2/2014 | Metzher et al. | | |
| 2014/0323340 A1 | 10/2014 | Goldberg et al. | | |

FOREIGN PATENT DOCUMENTS

KR 10-2007-0033685 A 3/2007

OTHER PUBLICATIONS

Fesenko et al. "Biosensing and monitoring of cell populations using the hydrogel bacterial microchip", Biosens Bioelectron. 2005, 20, pp. 1860-1865.*
James H. Jorgensen et al, Antimicrobial Susceptibility Testing: A Review of General Principles and Contemporary Practices, Medical Microbiology, 2009:49, pp. 1749-1755.
James Q. Boedicker et al, Detecting bacteria and determining their susceptibility to antibiotics by stochastic confinement in nanoliter . . . , Lab Chip, 2008, pp. 1265-1272.
Chia Hsiang Chen et al, Antimicrobial Susceptibility Testing Using High Surface-to-Volume Ratio Microchannels, Anal, Chem., 2010, pp. 1012-1019.
Ye-Jin Eun et al, Encapsulating Bacteria in Agarose Microparticles Using Microfluidics for High-Throughput Cell Analysis and Isolation, ACS Chem. Biol. 2011, pp. 260-266.
Keun Pil Kim et al, In situ monitoring of antibiotic susceptibility of bacterial biofilms in a microfluidic device, Lab Chip, 2010, pp. 3296-3299.
Ingmar Peitz et al, Single-cell bacteria growth monitoring by automated DEP-facilitated image analysis, Lab Chip, 2010, pp. 2944-2951.
Cheng-Che Chung et al, Antibiotic susceptibility test based on the dielectrophoretic behavior of elongated . . . AIP Biomicrofluidics, 2011, American Intitute of Physics.
Irene Sinn et al, Asynchronous magnetic bead rotation (AMBR) biosensor in microfluidic droplets for rapid bacterial growth and susceptibility . . . , Lab Chip, 2011, pp. 2604-2611.
Songmiao Liang et al, Protein diffusion in agarose hydrogel in situ measured by improved refractive index method, Journal of Controlled Release, 2006, pp. 189-196.
Derek C. Angus et al, Epidemiology of severe sepsis in the United States: Analysis of incidence, outcome, and associated costs of care, Crit Care Med 2001, pp. 1303-1310.

(Continued)

*Primary Examiner* — Vera Afremova
(74) *Attorney, Agent, or Firm* — STIP Law Group, LLC

(57) ABSTRACT

A testing method is disclosed. The testing method includes: providing a mixture solution of a gelling agent and a microbe to a gelling device; solidifying the mixture solution to form a solid thin film in which the microbe is immobilized; supplying a bioactive agent to the solid thin film and allowing the bioactive agent to diffuse into the solid thin film; and imaging the individual responses of the single microbial cells to the bioactive agent, and determining the minimum inhibitory concentration (MIC) of the bioactive agent based on the analysis of the images to obtain AST results.

21 Claims, 26 Drawing Sheets

(56) References Cited

OTHER PUBLICATIONS

Gregory G. Anderson et al, Intracellular Bacterial Biofilm-Like Pods in Urinary Tract Infections, Sicence vol. 301, 2003, pp. 105-107.
Phillip H. Gallo, PhD et al, Demonstration of Bacillus cereus in Orthopaedic-Implant-Related Infection with Use of a Multi-Primer . . . J Bone Joint Surg Am, 2011, e85(1-6).
Hirofumi Tani et a l. "Chip-based bioassay using bacterial sensor strains immobilized in three-dimensional micro-fluidic network". Anal. Chem. 2004, 76, 6693-6697.

* cited by examiner

FIG. 5
(a)
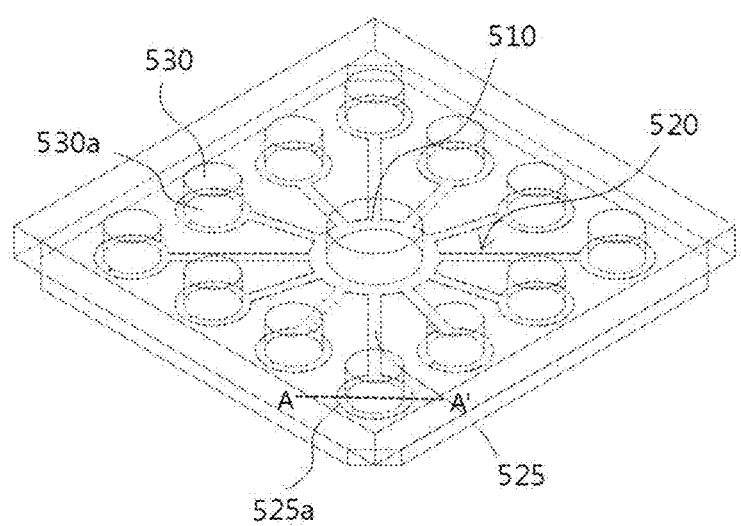
(b)
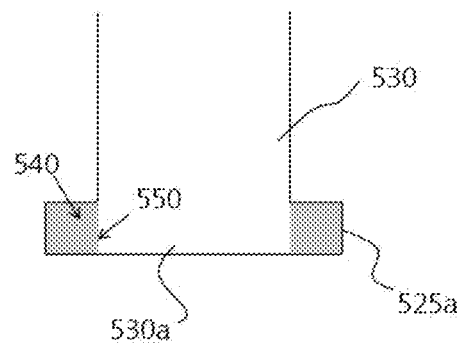

FIG. 6
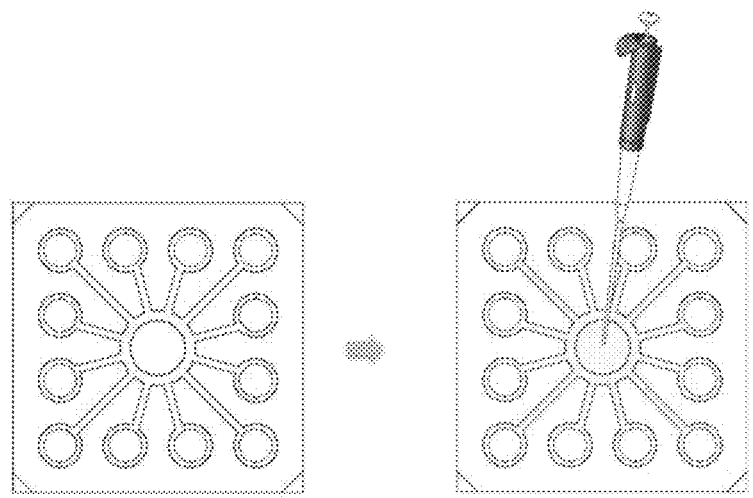
Injection of bacteria and gelling
agent-containing liquid medium
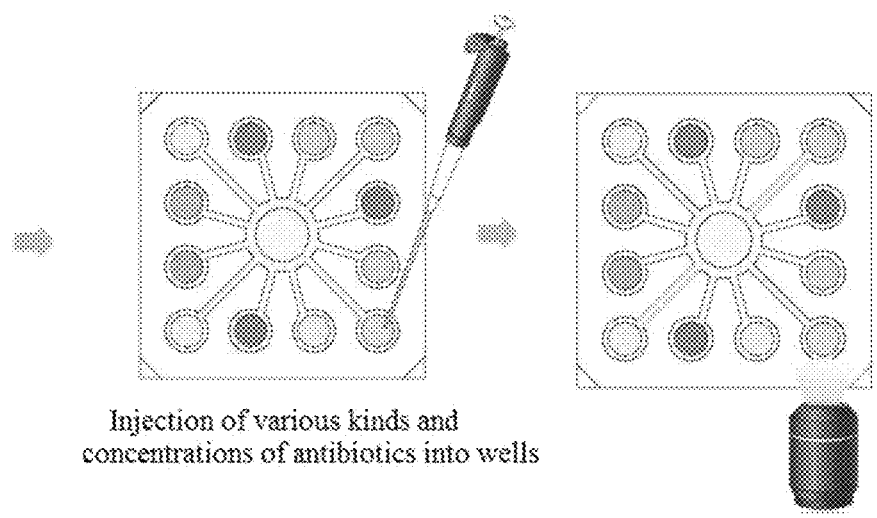
Injection of various kinds and
concentrations of antibiotics into wells
Observation and analysis of bacterial cell growth
through automated image processing system FIG. 20
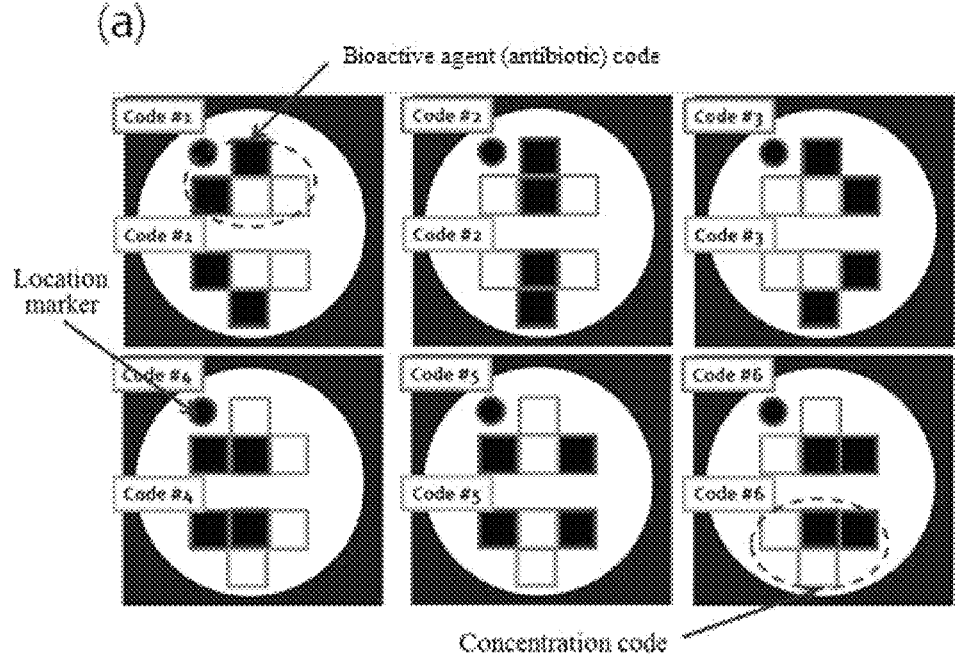
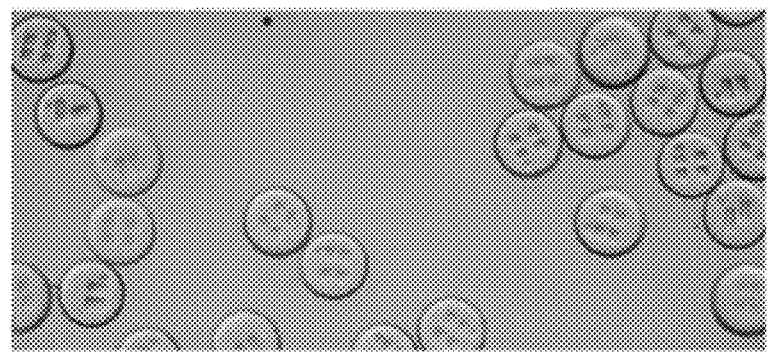

RAPID ANTIBIOTIC SUSCEPTIBILITY TESTING SYSTEM BASED ON BACTERIAL IMMOBILIZATION USING GELLING AGENT, ANTIBIOTIC DIFFUSION AND TRACKING OF SINGLE BACTERIAL CELLS

CROSS REFERENCE TO PRIOR APPLICATIONS

This application is a continuation application of U.S. patent application Ser. No. 13/756,872 filed Feb. 1, 2013, which claims priority to U.S. Provisional Application Ser. No. 61/593,407 filed Feb. 1, 2012 and Korean Patent Application No. 10-2012-0011002 filed Feb. 2, 2012, which are hereby incorporated by reference in their entirety.

BACKGROUND

The present invention generally relates to a rapid antibiotic susceptibility testing (RAST) system based on bacterial immobilization using a gelling agent, antibiotic diffusion, and tracking of single bacterial cells.

In general, the responses of cells to a drug are observed by placing the cells in a multi-well plate, injecting the drug in the form of a liquid, and monitoring time-dependent changes of the cells using an optical measurement system to obtain statistic results. As an antibiotic susceptibility testing method in a solid medium, the Kirby-Bauer (KB)-testing method, in which bacteria are scattered over an agar medium, antibiotic-absorbed papers are placed thereon and bacterial growth is observed, is known. In the case of microdilution testing in liquid media, a number of automated systems, such as VITEK2, Microscan and Phoenix, have been developed for antibiotic susceptibility testing. Such a system can be used for antibiotic susceptibility testing by placing an antibiotic in millimeter-sized wells, injecting bacteria, together with a liquid medium, into the wells, and statistically monitoring and determining the bacterial growth through turbidity.

Sepsis is one of the major causes of death in the US, necessitating rapid treatment with proper antibiotics. Roughly 750,000 patients contract severe sepsis each year in U.S. hospitals, and over 25% of them do not survive (Angus et al. (2001), Critical Care Medicine-Baltimore-, 29, 1303-1310). Conventional systems for antibiotic susceptibility testing (AST) take far too long (16-24 hr) for the timely treatment of sepsis.

When the responses of cells to different drugs are tested using the conventional systems, the cells are placed in a liquid or solid medium, the drugs are mixed with the liquid medium or drug-absorbed paper disks are placed on the solid medium to allow the cells to respond to the drugs, and the cell growth responses to the drugs are determined by turbidity (absorbance) measurement. However, such an approach is dependent on the collection of statistically valid data rather than on changes of single cells, and requires a long incubation time (usually 16-24 hours) because a predetermined number of cells should grow (usually one million cells per ml) in order to obtain statistic results. In this case, it is impossible to monitor changes occurring in single cells against drugs and monitor motile single cells in real time. Further, a great deal of time and labor is required to test the large number of drugs because the individual drugs are injected separately. The KB-test for antibiotic susceptibility testing in solid media basically requires a large number of agar medium plates to test the susceptibility of tens of antibiotics due to the limited number of the drugs that can be placed on the solid media. VITEK, an automated system developed to minimize testing time, also requires a relatively long time of about 12 hours because the turbidity of bacteria should increase above a predetermined level. Further, since environments for the conventional testing methods are different from in vivo environments, there may be many substantial differences between the test results and phenomena occurring in vivo (Gregory G. Anderson, et al. (2003), "Intracellular Bacterial Biofilm-Like Pods in Urinary Tract Infections", Science 301, 105; Gallo et al. (2011), "Demonstration of Bacillus cereus in Orthopaedic-Implant-Related Infection with Use of a Multi-Primer Polymerase Chain Reaction-Mass Spectrometry Assay.", J Bone Joint Surg Am, 93).

SUMMARY

According to one aspect of the present invention, there is provided a testing method including: providing a mixture solution of a gelling agent and a microbe to a gelling device; solidifying the mixture solution to form a solid thin film in which the microbe is immobilized; supplying a bioactive agent to the solid thin film and allowing the bioactive agent to diffuse into the solid thin film; and imaging the individual responses of the single microbial cells to the bioactive agent, and determining the minimum inhibitory concentration (MIC) of the bioactive agent based on the analysis of the images to obtain AST results.

According to another aspect of the present invention, there is provided a testing method including: providing a microfluidic channel system having a first microfluidic channel for cell fixation and a second microfluidic channel for supply of a bioactive agent, the two structures being in contact with each other in at least one area; providing a mixture solution of a gelling agent and a microbe to the first microfluidic channel wherein the flow of the mixture solution is controlled so that the mixture solution is prevented from bursting into the second microfluidic channel through the contact area; solidifying the mixture solution to form a microbe-immobilized solid thin film in the first microfluidic channel; supplying a bioactive agent to the second microfluidic channel and allowing the bioactive agent to flow to form an interface between the bioactive agent and the solid thin film in the contact area; allowing the bioactive agent to diffuse into the solid thin film through the interface; and imaging the individual responses of the single microbial cells to the bioactive agent, and analyzing the images.

According to another aspect of the present invention, there is provided a testing method including: providing a gelling device having a microfluidic channel and a well in contact with each other in at least one area; providing a mixture solution of a gelling agent and a microbe to the microfluidic channel; solidifying the mixture solution to form a microbe-immobilized solid thin film in the microfluidic channel; supplying a bioactive agent to the well to form an interface between the bioactive agent and the solid thin film in the contact area; allowing the bioactive agent to diffuse into the solid thin film through the interface; and imaging the individual responses of the single microbial cells to the bioactive agent, and analyzing the images.

According to another aspect of the present invention, there is provided a testing device including: a thin film formed by solidifying a mixture of a gelling agent and a microbe; and wells or microwells corresponding to the wells of a commercial multi-well plate.

According to another aspect of the present invention, there is provided a testing device including a thin film formed by solidifying a mixture of a gelling agent and a microbe wherein the thin film is formed in a microfluidic channel.

According to another aspect of the present invention, there is provided a testing device including a thin film formed by solidifying a gelling agent-containing liquid medium wherein the testing device takes the form of a microplate.

According to another aspect of the present invention, there is provided a testing system including: a testing device including a thin film formed by solidifying a mixture of a gelling agent and a microbe; a bioactive agent carrier for supplying a bioactive agent to the testing device; a stage for supporting and observing the testing material; and an analyzing system for observing the individual changes of the microbe caused by the delivery of the bioactive agent diffused from the bioactive agent carrier.

According to another aspect of the present invention, there is provided a method for fabricating a testing device, the method including: preparing a cover and a plate mold which is assembled and dissembled with the cover, the cover and the plate mold being designed to form an assembly having a plate-like internal space corresponding to the thickness of a thin film when coupled to each other; coupling the cover to the plate mold to form an assembly having at least one opening; injecting a mixture solution of a gelling agent-containing liquid medium and a microbe into the internal space through the opening; solidifying the mixture solution to form a solid thin film in which the microbe is immobilized; and separating the plate mold having the solid thin film from the assembly to obtain a microplate.

According to another aspect of the present invention, there is provided a testing method including: preparing a plurality of coded bioactive agent carriers containing one or more kinds of bioactive agents and distinguished from each other by the kind of the bioactive agents; providing the coded bioactive agent carriers to a testing device having a microbe-containing solid thin film; reading the codes of the bioactive agent carriers arranged at particular locations on the testing device; and analyzing the individual changes of the microbe present at the particular locations caused by the diffusion of the bioactive agents.

According to another aspect of the present invention, there is provided a testing system including: a thin film-like testing device fabricated by solidifying a mixture of a gelling agent-containing liquid medium and a microbe; coded bioactive agent carriers for supplying bioactive agents to the testing device; and an analyzing system for reading the codes of the bioactive agent carriers according to the location information of the testing device and observing the individual changes of the microbe caused by the delivery of the bioactive agents diffused from the coded bioactive agent carriers.

According to another aspect of the present invention, there is provided a testing method including: providing a microplate having a solid thin film in which a microbe is immobilized; supplying a bioactive agent to the solid thin film and allowing the bioactive agent to diffuse into the solid thin film; and imaging the individual responses of the single microbial cells to the bioactive agent, and analyzing the images.

According to yet another aspect of the present invention, there is provided a testing method including: bringing a microbe-immobilized agar- or agarose-based solid thin film into contact with a bioactive agent to deliver the bioactive agent to the solid thin film by diffusion; and tracking the individual changes in the microbial single cell growth against the bioactive agent. The growth changes may be tracked using an optical measurement system. The microbe may be selected from the group consisting of viruses, bacteria, archaea, protozoa, fungi, algae, green algae, rotifers, planarians, parasitic pathogens and biofilms.

BRIEF DESCRIPTION OF THE DRAWINGS

These and/or other aspects and advantages of the invention will become apparent and more readily appreciated from the following description of the embodiments, taken in conjunction with the accompanying drawings of which:

FIG. 5 shows a gelling device for fabricating a testing device according to one modification of the present invention;

FIG. 6 shows one embodiment of a method for simultaneously testing a number of antibiotics using a testing device with a microfluidic agarose channel (MAC) system;

FIG. 20 shows coded microparticles as coded bioactive agent carriers for multiplexing assay according to one embodiment of the present invention;

DETAILED DESCRIPTION

Figure 1:
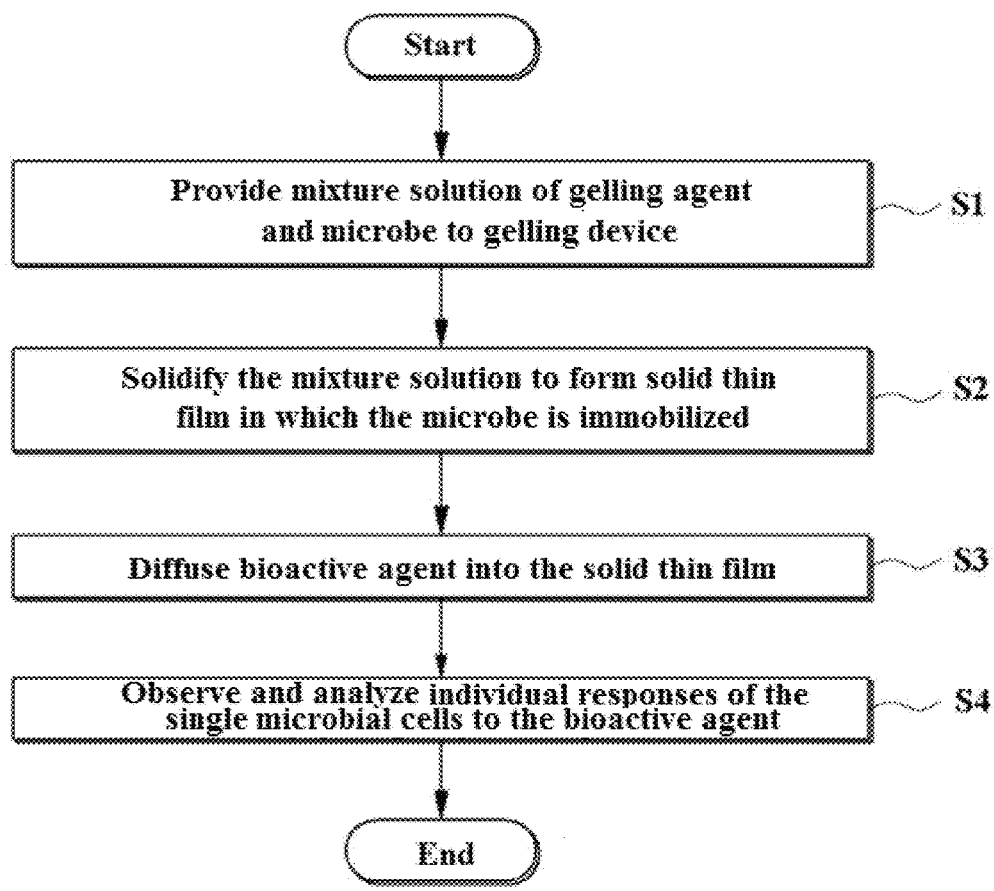
FIG. 1 is a process flowchart showing a testing method according to one embodiment of the present invention.

Embodiments of the present invention will now be described in more detail with reference to the accompanying drawings. However, the present invention is not limited to the embodiments set forth herein and may be embodied in many different forms. Rather, these embodiments are provided so that this disclosure is thorough and complete, and will fully convey the scope of the invention to those skilled in the art. In the drawings, the sizes, such as widths and thicknesses, of elements may be exaggerated for clarity. The drawings are explained from an observer's point of view. It will be understood that when an element is referred to as being "on" another element, it can be directly on the other element or one or more intervening elements may also be present therebetween. Those skilled in the art will appreciate that many modifications and variations can be made without departing from the spirit of the invention. Throughout the accompanying drawings, the same reference numerals are used to designate substantially the same elements.

On the other hand, terms used herein are to be understood as described below. While such terms as "first" and "second," etc., may be used to describe various elements, such elements must not be limited to the above terms. The above terms are used only to distinguish one element from another. For example, a first element may be referred to as a second element, and likewise a second element may be referred to as a first element.

As used herein, the singular forms "a", "an" and "the" are intended to include the plural forms as well, unless the context clearly indicates otherwise. It will be further understood that the terms "include(s)", "including", "have (has)" and/or "having", when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Respective steps of the methods described herein may be performed in a different order than that which is explicitly described. In other words, the respective steps may be performed in the same order as described, simultaneously, or in a reverse order.

The present invention provides testing methods including diffusing bioactive agents through solid thin films in which cells are immobilized, imaging the individual responses of the single cells to the bioactive agents, and determining the minimum inhibitory concentrations (MICs) of the bioactive agents based on the analysis of the images to obtain AST results. In the methods of the present invention, the solid thin films are formed using gelling devices in various forms. The present invention also provides various testing devices. The present invention also provides testing systems, each of which includes a testing device, a bioactive agent carrier, and an optical measurement unit.

Specifically, the present invention provides a testing method including the following steps. FIG. 1 is a process flowchart showing a testing method according to one embodiment of the present invention. Referring to FIG. 1, in step S1, a mixture solution of a gelling agent-containing liquid medium and a microbe is provided to a gelling device.

Water accounts for at least about 95% of the liquid medium. The liquid medium can be solidified due to the presence of the gelling agent. As the gelling agent, there may be exemplified agar, agarose, gelatin, alginate, collagen, or fibrin. The use of agar or agarose is preferred. For example, agar may be used in an amount of 0.5 to 4% by weight in the liquid medium. The liquid medium usually requires no nutrients. In some examples, however, the liquid medium may include nutrients.

Examples of microbes suitable for use in the testing method include viruses, bacteria, archaea, protozoa, fungi, algae, green algae, rotifers, planarians, parasitic pathogens and biofilms. Preferably, the microbes may be bacteria.

The microbe may grow in a liquid or solid medium, and the growth thereof may be affected by the kind and concentration of a foreign bioactive agent. The density of the microbe in the mixture solution is from $10^2$ to $10^{10}$ cells/ml, preferably from $10^4$ to $10^{10}$ cells/ml, more preferably from $10^5$ to $10^9$ cells/ml. If the density of the microbe is below the lower limit, it may be difficult to perceive the location of the microbe. Meanwhile, if the density of the microbe exceeds the upper limit, it may be difficult to perceive the individuals microbial state.

The gelling device may be a light-transmitting substrate, which is desirable in terms of optical imaging. The gelling device is not particularly limited so long as it has surface characteristics suitable for the formation of a thin film by the application of the liquid medium. Preferably, the gelling device has at least one receiving portion having an internal space where the liquid medium is retained. The receiving portion may take the form of a microwell, a narrow flat recess, a microfluidic channel, or a combination thereof. The liquid medium is fed into the gelling device through the receiving portion and undergoes solidification. The form of the receiving portion determines the shape of a solid thin film in the subsequent step. The receiving portion has a depth to determine the thickness of the solid thin film. The depth of the receiving portion (i.e. the well or channel depth, or the recess spacing) may be in the range of 1 μm to 5 mm, 1 μm to 3 mm, 1 μm to 2 mm, 1 μm to 1.5 mm, 1 μm to 1 mm, 1 μm to 800 μm, 1 μm to 500 μm, 1 μm to 100 μm, 10 μm to 3 mm, 10 μm to 1 mm, 100 μm to 1 mm, 200 μm to 1 mm, or 500 μm to 1 mm.

The receiving portion may take the form of a microwell. In this case, the microwell typically has a width (diameter) not larger than 10 mm, for example, from several tens of micrometers to several millimeters. Alternatively, the receiving portion may take the form of a narrow flat recess. In this case, for example, the plate may have a width corresponding to the size of a slide glass (about 75 mm×25 mm). Alternatively, the receiving portion may take the form of a microfluidic channel. In this case, the channel may have a width of 10 µm to 1 mm, preferably 10 µm to 500 µm.

In step S2, the mixture solution is solidified to form a solid thin film in which the microbe is immobilized. As the temperature of the liquid medium is decreased from a higher temperature, the medium is solidified, which inhibits the mobility of the microbe. This immobilization facilitates continuous observation of the motile microbe.

The thickness and width of the solid thin film are determined depending on the depth and width of the receiving portion. The term "thin film" used herein refers to a thin layer that has a thickness sufficient to immobilize the microbe and to observe the single cells. The thickness of the thin film is typically in the range of 1 µm to 5 mm, 1 µm to 3 mm, 1 µm to 2 mm, 1 µm to 1.5 mm, 1 µm to 1 mm, 1 µm to 800 µm, 1 µm to 500 µm, 1 µm to 100 µm, 10 µm to 3 mm, 10 µm to 1 mm, 100 µm to 1 mm, 200 µm to 1 mm, or 500 µm to 1 mm, but is not particularly limited to this range. The thickness of the solid thin film may correspond to the size of a side of the solid thin film in a direction perpendicular to a side of the solid thin film to be observed. Within the thickness range of the solid thin film defined above, the single microbial cells immobilized in the solid thin film can be observed.

The microbe-immobilized solid thin film itself or the gelling device having the microbe-immobilized solid thin film is referred to as a "testing device" in the present specification. The testing device may exist in various forms depending on the shape of the substrate.

In step S3, a bioactive agent is supplied to the solid thin film and is allowed to diffuse into the solid thin film. The bioactive agent may include a substance selected from drugs, such as antibiotics, anticancer agents and immunosuppressants, nutrients, cellular secretions, signal transducers, viruses, cells, micro RNAs, proteins, antigens, antibodies, and DNA.

In step S4, the individual responses of the single microbial cells to the bioactive agent are imaged, and the minimum inhibitory concentration (MIC) of the bioactive agent is determined based on the analysis of the images to obtain AST results.

The microbe is immobilized and distributed two-dimensionally in the solid thin film, and as a result, the single microbial cells can be observed. According to the testing method, changes in the growth of the single microbial cells can be typically observed within several tens of minutes (normally 30 minutes). Accordingly, the testing method of the present invention allows for the identification of the effect of the bioactive agent on the microbe in a more accurate and rapid manner than conventional testing methods. For example, the testing method of the present invention for the bioactivity of bacterial cells can be completed within 3-4 hours.

An optical measurement system may be used for observation. The optical measurement system may include an imaging system, such as a CCD or CMOS camera. The optical measurement system may include optical units or devices necessary for focusing and light imaging, such as a lens, an illuminator, and a light guide. The optical measurement system may include an image processing system for processing and analyzing image data observed by the imaging system. The optical measurement system rapidly records and analyzes changes in the growth of the microbe observed during testing to obtain test results.

Consequently, the use of the testing method based on the immobilization of the microbe and the diffusion of the bioactive agent can greatly reduce the amounts of drugs and cells necessary for drug testing, and enable rapid tracking of changes in the growth of single cells to obtain test results on the drugs as rapidly as 2 hours (normally within 3-4 hours), compared to the prior art. This is the most rapid testing speed known thus far.

The testing method of the present invention employs testing devices in various forms that include microbe-immobilized solid thin films.

According to one embodiment of the present invention, a testing system is provided. The testing system includes: a thin film-like testing device fabricated by solidifying a mixture of a gelling agent-containing liquid medium and a microbe; a bioactive agent carrier for supplying a bioactive agent to the testing device; and an optical measurement system for observing the individual changes of the single microbial cells caused by the delivery of the bioactive agent diffused from the bioactive agent carrier. The bioactive agent carrier is not particularly limited so long as it can receive and release the bioactive agent. Examples of such bioactive agent carriers include test tubes, multi-well plates, microfluidic channels, and microparticles. The optical measurement system may include an imaging system adapted to create observed images, such as a CCD or CMOS camera. Further, the optical measurement system may include an image processing system for processing and analyzing the created images.

The testing device is not limited to a particular form so long as it includes a microbe-immobilized solid thin film and can deliver the bioactive agent to the microbe therein by diffusion. Representative examples of the testing device are broadly classified into the following three categories for the purpose of convenience, but various other examples are possible.

A first exemplary embodiment of the testing device according to the present invention may take the form of a microfluidic channel. The testing device includes a solid thin film that exists as a part of a microfluidic channel system and in which a microbe is immobilized. The microfluidic channel system may be formed, for example, by general soft-lithography.

The testing device in the form of a microfluidic channel may include a first microfluidic channel in which a microbe-immobilized solid thin film is formed and a second microfluidic channel in which a bioactive agent flows. The second microfluidic channel may be in direct or indirect contact with the first microfluidic channel in at least one area. The first microfluidic channel and the second microfluidic channel may exist on the same substrate or different substrates separated from each other. In one embodiment, the microfluidic channel system including the first and second microfluidic channels may have a side-branched radial structure. In an alternative embodiment, the microfluidic channel system may have a structure in which a membrane is interposed between a substrate on which the first microfluidic channel is formed and a substrate on which the second microfluidic channel is formed.

The bioactive agent is supplied through the second microfluidic channel to test the bioactivity thereof. At this time, the solid thin film in the first microfluidic channel and the bioactive agent form an interface in the contact area between the first and second microfluidic channels. Thereafter, the bioactive agent supplied from the second microfluidic channel can be diffused into the solid thin film in the first microfluidic channel through the interface. Next, the bioactivity of the bioactive agent can be tested by observing changes in the growth of the microbe in the solid thin film. The bioactive agent can be supplied by various methods, for example, applying a positive or negative pressure using a power pump, inclining the channel, forming a capillary tube in the channel, using a highly absorptive material, or using a water bath.

Figure 2:
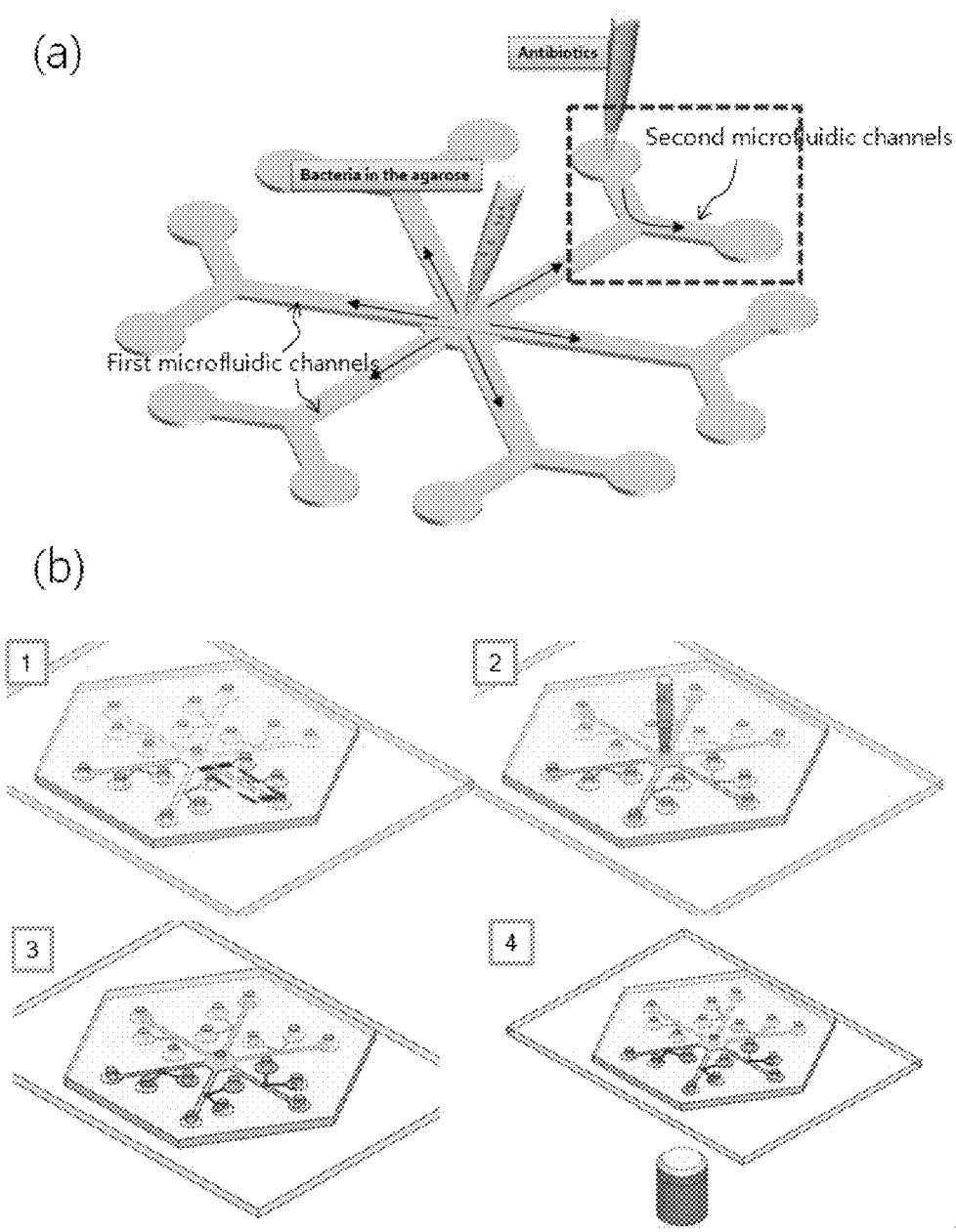
FIG. 2 shows a first exemplary embodiment of a testing device according to the present invention.

FIG. 2 shows the first exemplary embodiment of the testing device according to the present invention. Referring to FIG. 2, (a) shows a microfluidic channel system including six radially extending branches as first microfluidic channels (main channels) and second microfluidic channels (side-branched channels) in contact with the respective first microfluidic channels. When an agarose solution containing bacteria is introduced into the center of the radial structure, it flows and is injected into the branches of the empty main channels. Thereafter, the agarose solution is gelled to form an agarose solid thin film in which the bacteria are immobilized. Next, bioactivity testing can be conducted by supplying an antibiotic through the side-branched channels.

In FIG. 2, (b) shows the overall procedure of a bioactivity testing process using the microfluidic channels. The bioactivity testing process may include the following steps: 1) provision of the microfluidic channels; 2) injection of the liquid medium into which the microbe is introduced, and gelling of the liquid medium to form a solid thin film; 3) supply of the bioactive agent; and 4) observation using an optical measurement system.

The microbe-immobilized solid thin film is formed as a result of gelling of the gelling agent-containing liquid medium together with the microbe. For the formation of the solid thin film, it is necessary to inject a mixture solution of the gelling agent-containing liquid medium and the microbe into the first microfluidic channels. During the injection, the mixture solution may flow toward the second microfluidic channels in direct or indirect contact with the first microfluidic channels in at least one area. Thus, it is necessary to allow the mixture solution to flow only in the first microfluidic channels without bursting into the second microfluidic channels. The microfluidic system may further include anchors in the contact areas to prevent the mixture solution from bursting into the second microfluidic channels.

Figure 3:
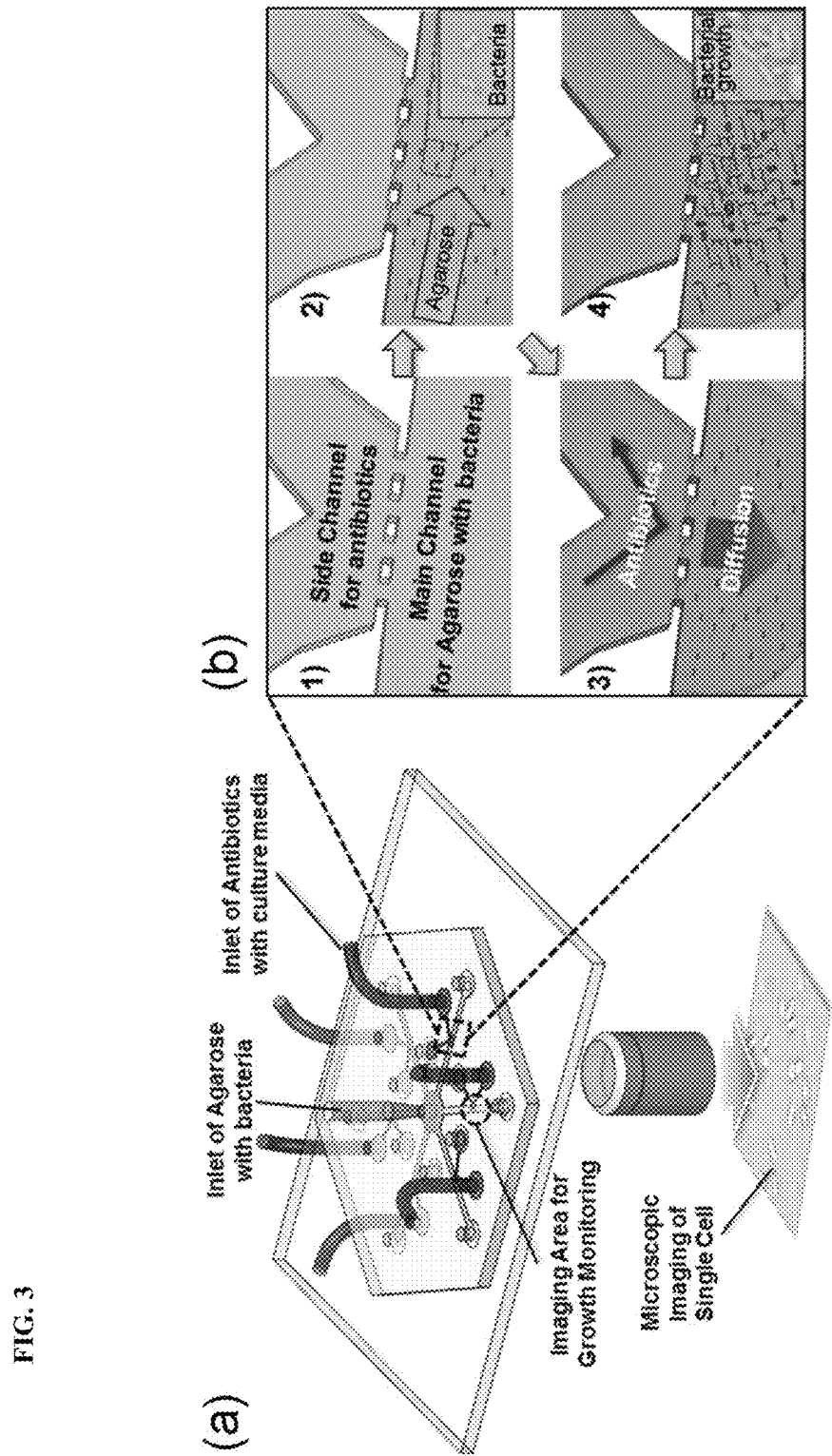
FIG. 3 schematically shows an antibiotic susceptibility testing (AST) process using a microfluidic agarose channel (MAC) chip.

FIG. 3 schematically shows an antibiotic susceptibility testing (AST) process using a microfluidic agarose channel (MAC) chip. Referring to (a) in FIG. 3, the MAC chip is fabricated by assembly of polydimethylsiloxane (PDMS) channels on a PDMS-coated glass substrate. The MAC chip has a size of about 20 mm×20 mm, which is similar to that of a coin. An agarose-bacteria mixture is injected into the center of the MAC chip and flows synchronously into the six main channels. An antibiotic is diluted with culture media and the antibiotic solutions at different concentrations are supplied to the side-branched channels. The interfaces between the agarose with bacteria and the antibiotic solutions are monitored using a microscope to analyze the bacterial cell growth. 1) to 4) in (b) are enlarged diagrams showing the bioactivity testing process. 1) shows the empty channels before antibiotic susceptibility testing (AST), 2) shows the introduction of the agarose-bacteria mixture into the main channels, 3) shows the formation of interfaces due to anchors and the introduction and diffusion of different concentrations of the antibiotic into the main channels through the six side-branched channels, and 4) shows tracking of the bacterial cell growth by a time-lapse method using a microscope.

When a liquid medium containing a gelling agent, such as agarose, is introduced into the main channels, it is necessary to prevent the liquid medium from bursting into the side-branched channels in which the antibiotic is present. To this end, the dimensions of the anchors and the gaps between the anchors are optimized such that proper interfaces are formed in the channels.

Figure 4:
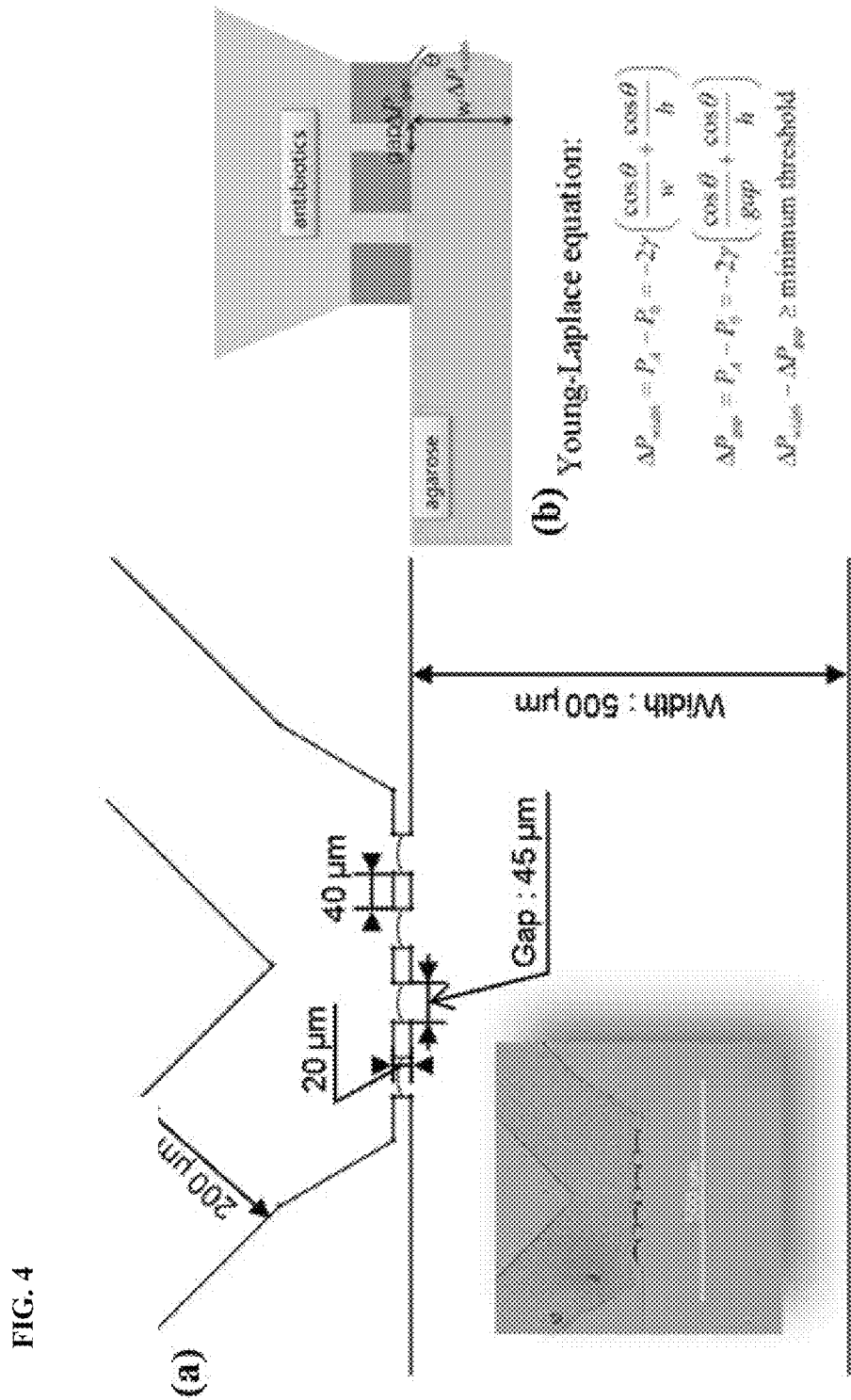
FIG. 4 is a diagram showing a state in which agarose with bacteria forms an interface by anchors.

FIG. 4 is a diagram showing a state in which agarose with bacteria forms an interface by anchors. (a) in FIG. 4 is an example showing proper dimensions of the channels and the anchors, and the inset shows an example of an actual interface formed by the anchors. (b) in FIG. 4 shows a Young-Laplace equation used for the formation of a proper interface.

According to one modification of the first exemplary embodiment, there is provided a testing device that is fabricated using a gelling device including wells instead of the second microfluidic channels.

FIG. 5 shows a gelling device for fabricating the testing device according to one modification of the present invention. In FIG. 5, (a) is a perspective view of the gelling device and (b) is a cross-sectional view taken along line A-A' of (a). Referring to FIG. 5, the gelling device 500 is wholly made of a light-transmitting material (for example, polystyrene) and has a microfluidic channel system 520 into which a liquid medium can flow through an inlet 510. The microfluidic channel system 520 consists of radially extending sub-channels 525. The gelling device 500 has a number of wells 530 on the upper side thereof. For example, bioactive agents may be injected through inlets of the wells 530. The ends 525a of the sub-channels 525 are in communication with the lower ends 530a of the wells 530 to form open channels. Thereafter, each of the bioactive agents meets a solid thin film 540 formed by solidification of the liquid medium to form an interface 550. Hydrophilization of the microfluidic channels stably maintains the interfaces 550 by cohesion and hydrophilicity even after injection of the liquid medium, as shown in (b).

Preferably, the ends 525a of the sub-channels 525 form ring-shaped open channels surrounding the wells 530. In this case, the interfaces 550 have larger areas. The gelling device 500 can be used to simultaneously test various kinds and concentrations of bioactive agents due to the presence of a large number of the radial sub-channels 525.

According to one embodiment of the present invention, there is provided a gelling device including a microfluidic channel and a well in contact with each other in at least one area. Next, a mixture solution of a gelling agent-containing and a microbe is provided to the microfluidic channel. The microfluidic channel may be hydrophilized, for example, by plasma treatment. By this hydrophilization, the flow of the mixture solution is controlled so that the mixture solution can be prevented from bursting into the well through the contact area. Next, the mixture solution is solidified to form a microbe-immobilized solid thin film in the microfluidic channel. Next, a bioactive agent is supplied to the well and meets the solid thin film to form an interface in the contact area. Next, the bioactive agent is allowed to diffuse into the solid thin film through the interface. Subsequently, the bioactive agent can be tested by observing the individual responses of the microbe to the bioactive agent.

Figure 7:
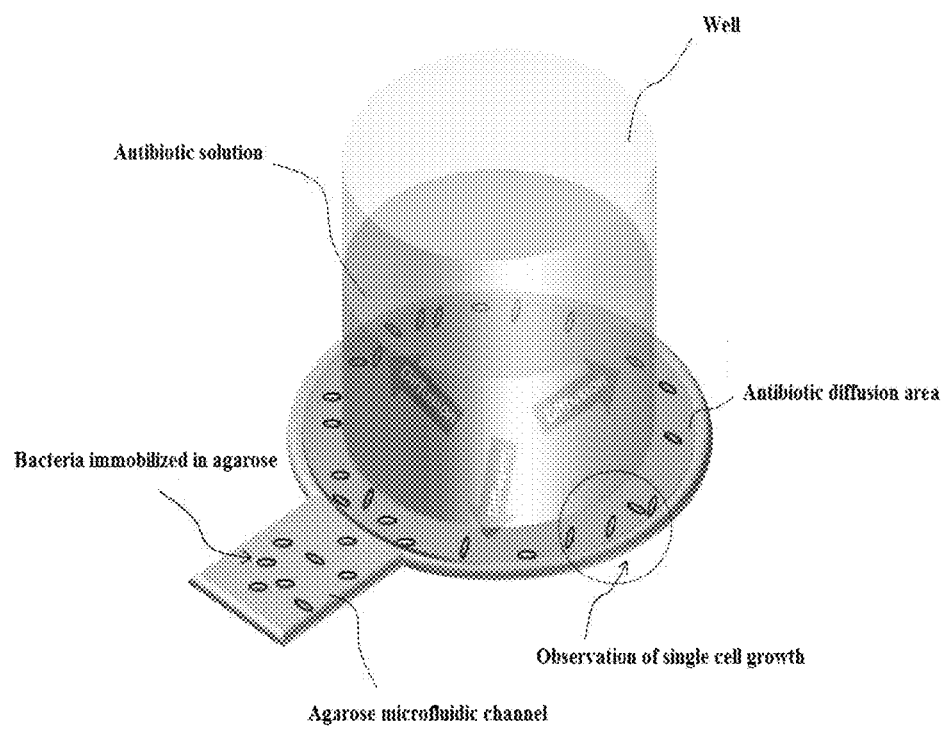
FIG. 7 is an enlarged diagram showing a portion of the testing device of FIG. 6 for AST.

FIG. 6 shows one embodiment of a method for simultaneously testing a number of antibiotics using a testing device with a microfluidic agarose channel (MAC) system. FIG. 7 is an enlarged diagram showing a portion of the testing device of FIG. 6 for AST. Referring to FIG. 7, antibiotic susceptibility testing can be conducted because the growth of single bacterial cells can be observed in areas where the antibiotics are diffused.

Figure 8:
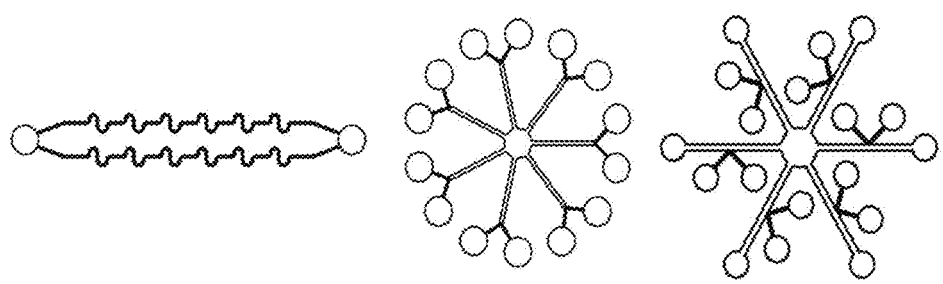
FIG. 8 shows some exemplary testing devices in the form of microfluidic channels.

The microfluidic channel system of the present invention may have various structures, as described above. FIG. 8 shows some exemplary testing devices in the form of microfluidic channels. The left diagram shows a membrane type testing device, the middle diagram shows a radial ('Y-shaped') testing device, and the right diagram shows another radial ('K-shaped') testing device.

Figure 9:
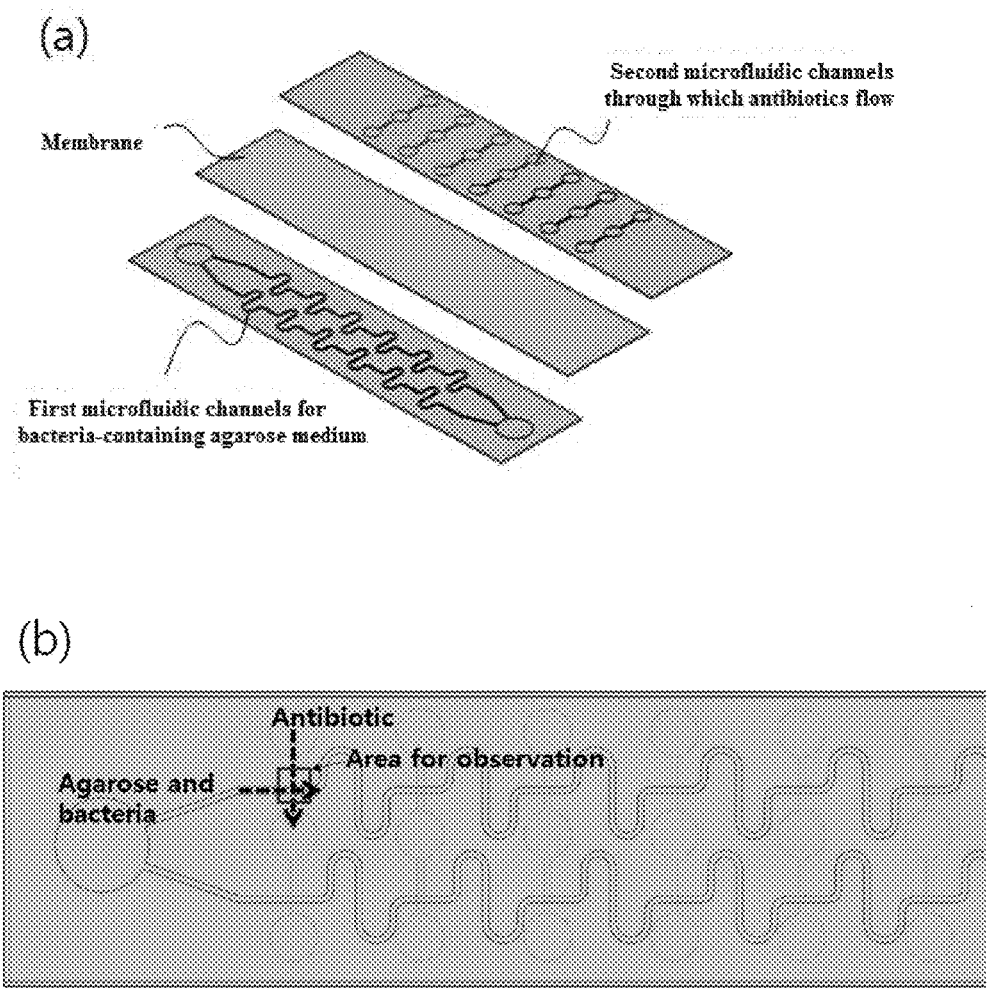
FIG. 9 shows diagrams for explaining a membrane type microfluidic channel system.

FIG. 9 shows diagrams for explaining the membrane type microfluidic channel system. (a) and (b) in FIG. 9 show an exploded perspective diagram and a plan view of the membrane type microfluidic channel system, respectively. The microfluidic channel system of FIG. 9 may have a laminate structure including a membrane. In this case, although the first microfluidic channels do not come into direct contact with the second microfluidic channels due to the presence of the membrane, the first and second microfluidic channels can be considered to be in indirect contact with each other through the membrane having many micropores because bioactive agents can be transported between the channels through the micropores of the membrane. The lowermost layer of the membrane type microfluidic channel system is filled with a mixture solution of agarose and bacteria. At this time, the agarose remains only in the lowermost layer because it is blocked by the membrane. The first microfluidic channels present in the underlying layer are bent so as to have larger lengths. This bending prevents the first microfluidic channels from being contaminated by the diffusion of the bioactive agents between the adjacent points of intersection. Next, antibiotics as the bioactive agents are allowed to flow through the second microfluidic channels present in the uppermost layer. The antibiotics are diffused through the membrane at the points where the two channels intersect. The agarose cannot pass through the membrane but the antibiotics can pass through the membrane by diffusion.

The use of the microfluidic channels can reduce the quantities of the microbe and the bioactive agents, thus enabling bioactivity testing at reduced cost. Another advantage associated with the use of the microfluidic channel system is that the responses of a single microbe to various kinds and concentrations of bioactive agents can be observed simultaneously.

The MAC system can be very useful for biofilm assay as well as antibiotic susceptibility testing. Biofilms are found in areas infected with microbes or to which microbes are attached. Biofilms refer to films that constitute mucilaginous microbial complexes, which are formed by microbes surrounded with polymer matrices. The formation of biofilms can greatly affect human health. Biofilms cause pulmonary infections, otitis media, periodontitis, and other infectious diseases. The resistance of bacteria present in biofilms against antibiotics is at least 1,000 times stronger than that of suspended bacteria. Flow cell systems and well-based systems have been used to investigate biofilms. However, these assay systems require a long time of several days for biofilm formation. Other difficulties associated with the use of the assay systems are the need to stain biofilms and the use of confocal microscopes for observation. Further experiments are needed for the measurement of minimum inhibitory concentration (MIC) or minimum biofilm eradication concentration (MBEC). Such systems are very large in size, and fail to clearly show biofilm formation stages and to represent in vivo biofilm formation.

Thus, there is a need for efficient systems that are suitable to investigate the formation of biofilms and the reactivity of biofilms with antibiotics. In consideration of this need, the MAC system according to one embodiment of the present invention proves to be an excellent alternative to conventional systems.

Figure 10:
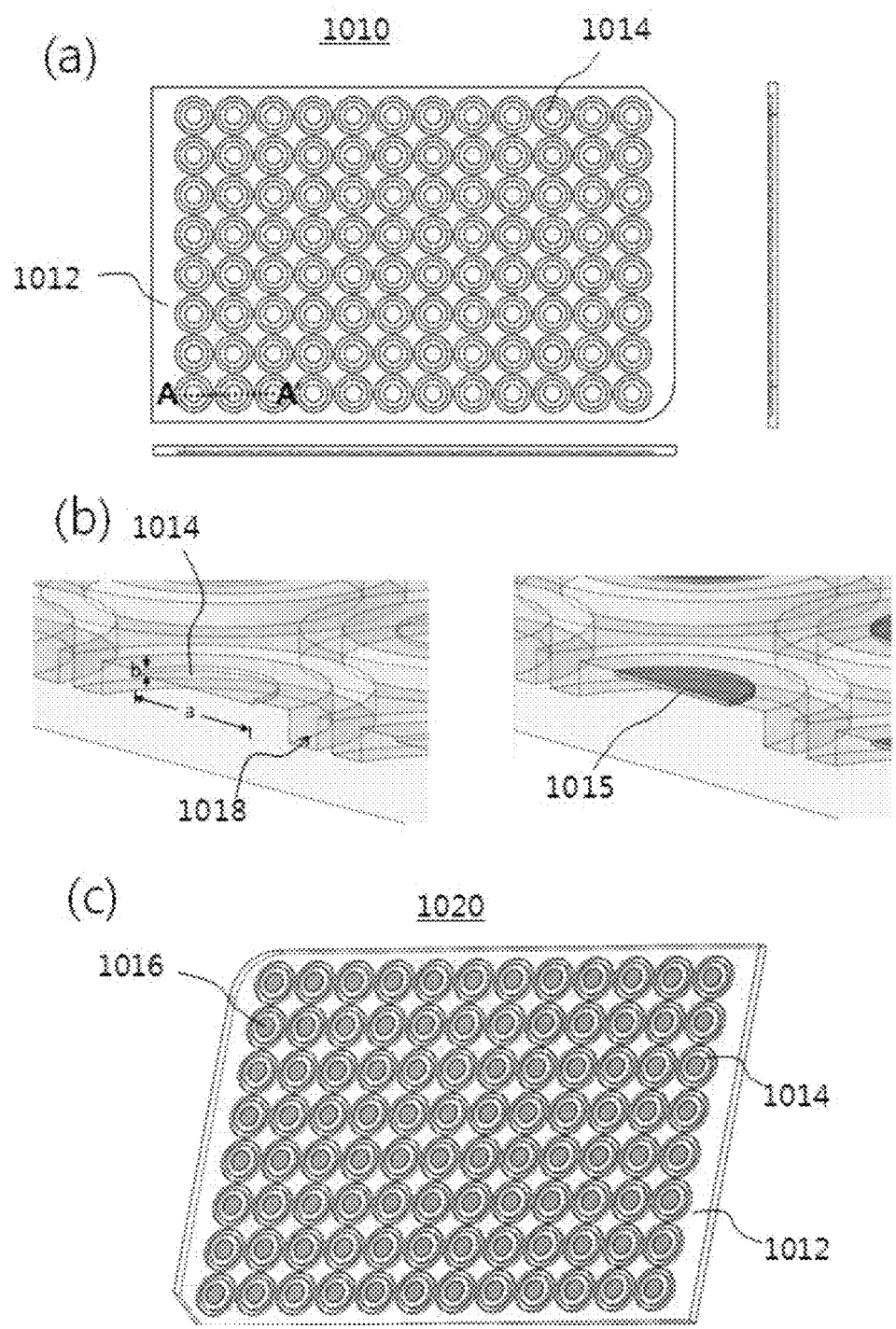
FIG. 10 shows a second exemplary embodiment of a testing device according to the present invention.

A second exemplary embodiment of the testing device according to the present invention may be in the form of a plate including a number of microwells. FIG. 10 shows the second exemplary embodiment of the testing device according to the present invention. In FIG. 10, (a) shows plan (left), side (right) and front (bottom) views of the testing device. A gelling device 1010 is required to fabricate the testing device 1020. The gelling device 1010 includes a body 1012 and one or more microwells 1014 arranged on the body 1012. The microwells 1014 serve as receiving parts. The body 1012 may be made of a light-transmitting material for ease of observation.

Each of the microwells 1014 of the gelling device 1010 has a depth sufficient to accommodate a mixture solution of a microbe and a liquid medium. Thereafter, the mixture solution is solidified to form thin film layers as solid media. (b) in FIG. 10 is an enlarged cross-sectional diagram of one of the microwells 1014, taken along line A-A' of (a). The left and right diagrams show states of the well 1014 before and after filling with the mixture solution 1015, respectively. The mixture solution 1015 is poured into the microwells 1014 of the gelling device 1010 and is solidified there. After a certain time, the substrate surface is swept to remove solids above a predetermined height and solids formed outside the wells.

The dimensions of the microwells 1014 have already been explained in step S1 of the foregoing embodiment. The depth a of the well is from 1 µm to 1 mm, preferably 1 µm to 500 µm, more preferably 1 µm to 100 µm, and the width b of the well is from 1 µm to 10 mm, preferably from 10 µm to 1 mm, more preferably from 10 µm to 100 µm. As a result of the solidification, solid thin films 1016 are formed and the microbes are immobilized therein.

The testing device has a structure in which the microbe-immobilized solid thin films 1016 are introduced into the gelling device 1010.

Multi-well plates are standard tools for treating and analyzing a large number of samples in chemical, biochemical and/or biological assays. Multi-well plates may take various forms, sizes and shapes. Generally, multi-well plates are produced to have standard sizes and shapes and have standard arrangements of wells. The standard arrangements of wells include those found in 96-well plates (12×8 array of wells), 384-well plates (24×16 array of wells), and 1536-well plates (48×32 array of wells). Multi-well plates having other arrangements of wells are commercially available.

In one embodiment, the testing device may include a number of microwells coupled to a multi-well plate in which bioactive agents are accommodated. The microwells are suitably aligned for use. For example, a commercially available 96-well plate or 384-well plate adapted to accommodate bioactive agents may be used. The gelling device 1010 may further include fastening parts 1018 to assist in coupling with the multi-well plate. Each of the fastening parts 1018 may have a convex-concave shape designed to engage with the upper end of the multi-well plate.

In FIG. 10, (c) shows the testing device 1020 fabricated by forming the solid thin films 1016 in the microwells 1014 of the gelling device 1010. The microbe in the solid media 1016 can be observed from the outside through the body 1012, which is preferably made of a light transmitting material as described above. The testing device 1020 may be coupled to the multi-well plate such that the microwells 1014 correspond to the wells of the multi-well plate while covering the upper portion of the multi-well plate including bioactive agents. The testing device 1020 shown in (c) is herein called "AgarPad."

Figure 11:
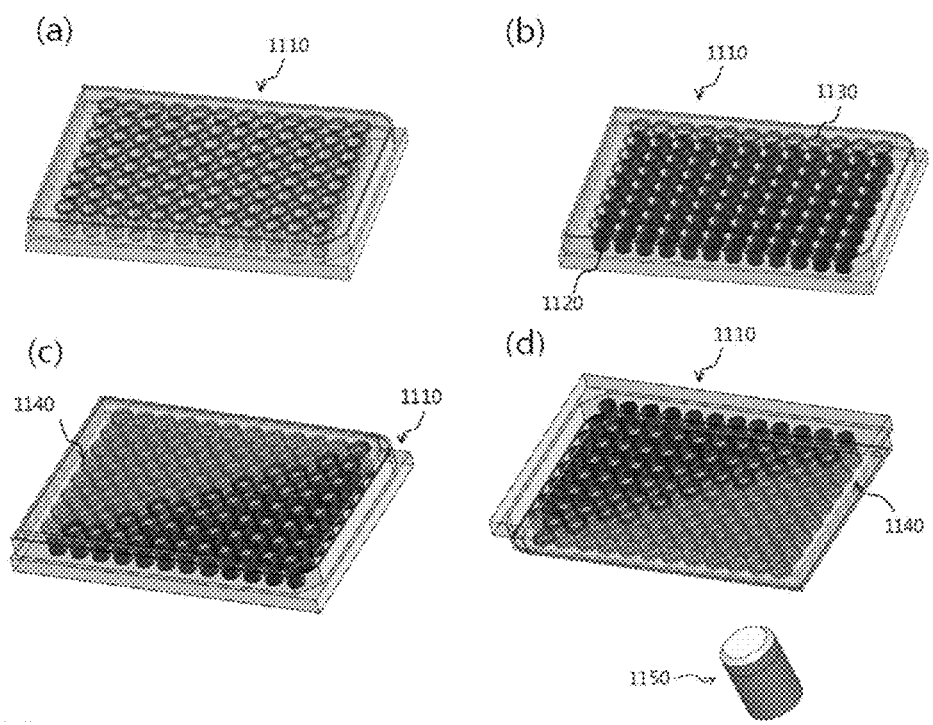
FIG. 11 shows an antibiotic susceptibility testing (AST) process using the testing device of FIG. 10 and a 96-well plate.

According to one embodiment, the testing device 1020 can be used for antibiotic susceptibility testing (AST). FIG. 11 shows an antibiotic susceptibility testing (AST) process using the testing device of FIG. 10 and a 96-well plate. Referring to (a) in FIG. 11, a general 96-well plate 1110 is prepared. Next, in (b), different kinds and concentrations of antibiotics 1120 are filled in the wells 1130. In (c), AgarPad 1140 containing bacteria-immobilized agarose is coupled to the 96-well plate 1110. Thereafter, in (d), the assembly is inverted such that the AgarPad 1140 is directed downward. As a result of the inversion, the antibiotics 1120 are moved to the AgarPad 1140 by gravity. The movement of the antibiotics 1120 may be promoted by the application of various external forces, including vortex mixing or centrifugation, other than gravity. Antibiotic susceptibility testing (AST) proceeds in such a way that the antibiotics 1120 are delivered to the bacteria through diffusion into the agarose solid media accommodated in the AgarPad 1140. From the beginning of diffusion of the antibiotics 1120, the bacterial growth process can be observed using an optical measurement system 1150.

Figure 12:
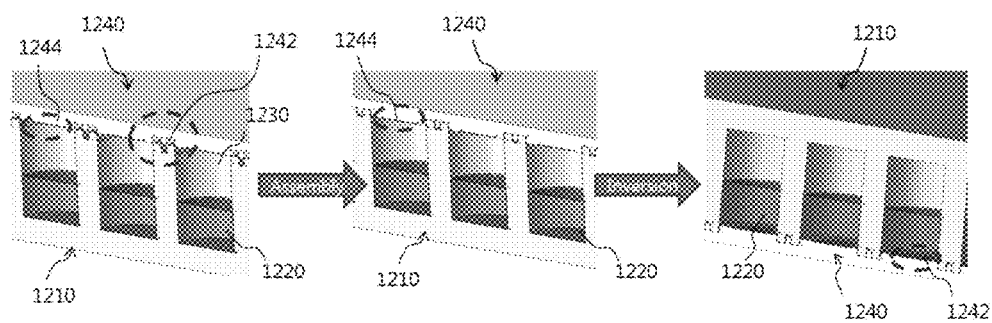
FIG. 12 is a more detailed diagram showing the initial stage of antibiotic susceptibility testing at which AgarPad is assembled with a 96-well plate and the assembly is inverted.

FIG. 12 is a more detailed diagram showing the initial stage of antibiotic susceptibility testing at which the AgarPad is assembled with the 96-well plate and the assembly is inverted. First, the 96-well plate 1210 accommodating the antibiotics 1220 in the wells 1230 is prepared. The AgarPad 1240 is fastened to the 96-well plate 1210 via coupling recesses 1242 to form an assembly in which the wells 1230 are sealed. After fastening, the assembly is fully inverted to bring the antibiotics 1220 into contact with agarose thin films 1244 in which bacterial cells located in the microwells of the AgarPad 1240 are immobilized. Thereafter, the antibiotics 1220 begin to diffuse into the agarose thin films 1244.

According to a further modification, there is provided a testing device based on microwells to which microfluidic channels are coupled. The testing device is similar to the plate including a number of microwells described in the first exemplary embodiment, except that microfluidic channels are coupled to microwells. The testing device uses, as a gelling device, a plate based on microwells to which microfluidic channels are coupled. The testing device may be fabricated by injecting gellable liquid media containing microbes into the microwells of the plate to form solid thin films. The testing device is similar to the testing device according to the first exemplary embodiment, a bioactivity testing process using the testing device is also substantially similar to that using the testing device according to the first exemplary embodiment, and thus detailed descriptions thereof are omitted. The only difference between the two testing devices is that mixture solutions of microbes and liquid media are injected through the microfluidic channels. If the mixture solutions are injected in an unsealed environment, there is the risk that the microbes may be exposed to humans. The injection of the mixture solutions through the microfluidic channels connected to the microwells prevents the microbes from being exposed to ambient environments. In addition, the necessary amounts of the mixture solutions to be injected to the microwells through the microfluidic channels can be appropriately calculated. Therefore, loss of the liquid media and the microbes can be minimized, contributing to cost reduction.

The testing device may have various designs on a single substrate depending on the formation method of the microfluidic channels in the gelling device. For example, a gelling device having 96 microwells, and then the testing device is designed such that six microfluidic channels are independently present, each of which is connected to 16 of the 96 microwells of the gelling device. Liquid media including six different kinds of microbes are injected into the microwells through the respective microfluidic channels, followed by gelling. As a result, the six different kinds of microbes are introduced into the testing device. In this case, bioactivity testing can be conducted simultaneously on 16 different kinds and concentrations of bioactive agents per microbe. That is, a maximum of 96 bioactivity tests are possible.

Figure 13:
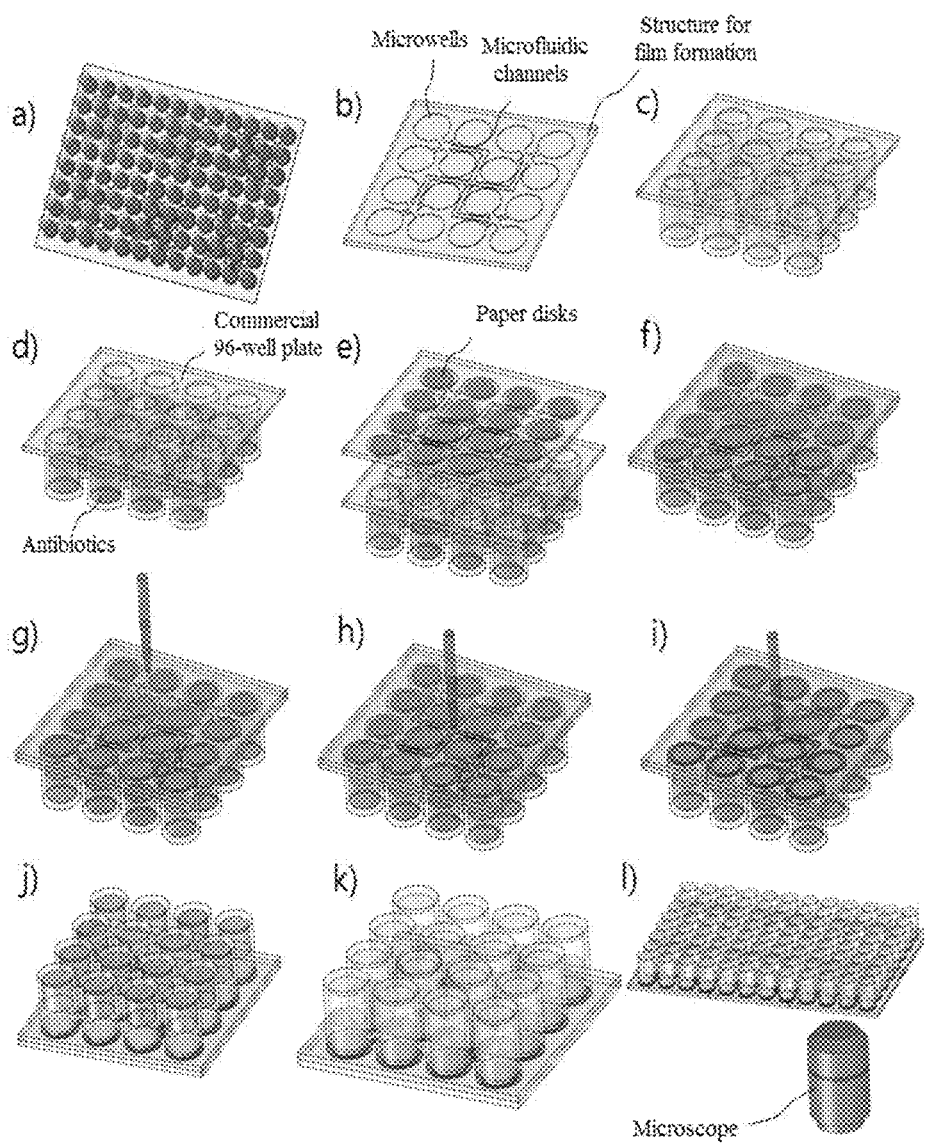
FIG. 13 shows a rapid antibiotic susceptibility testing (RAST) system using a microwell-based plate with microfluidic channels according to the present invention, and a testing process using the RAST system.

A commercially available multi-well plate whose wells correspond to the microwells of the testing device is coupled to the testing device for bioactivity testing. FIG. 13 shows a rapid antibiotic susceptibility testing (RAST) system using a microwell-based plate with microfluidic channels according to the present invention, and a testing process using the RAST system. In FIG. 13, a) shows the entire structure of the microwell-based plate including microfluidic channels, b) shows a gelling device including microfluidic channels and microwells formed by injection molding, c) shows a commercially available 96-well plate, d) shows the accommodation of various concentrations and kinds of antibiotics, e) shows alignment of the microwells with paper disks and the wells containing the antibiotics, f) shows an assembly of the gelling device and the 96-well plate, g) to i) show injection of agarose mixed with bacteria using a syringe, and gelling of the agarose, j) shows full inversion of the assembly, k) shows a downward flow of the antibiotics by gravity, penetration of the antibiotics through the paper disks, and diffusion of the antibiotics into the agarose, and l) shows microscopic observation. The paper disks assist in the formation of ring-shaped channels in the microwells and the diffusion of the antibiotics.

Figure 14:
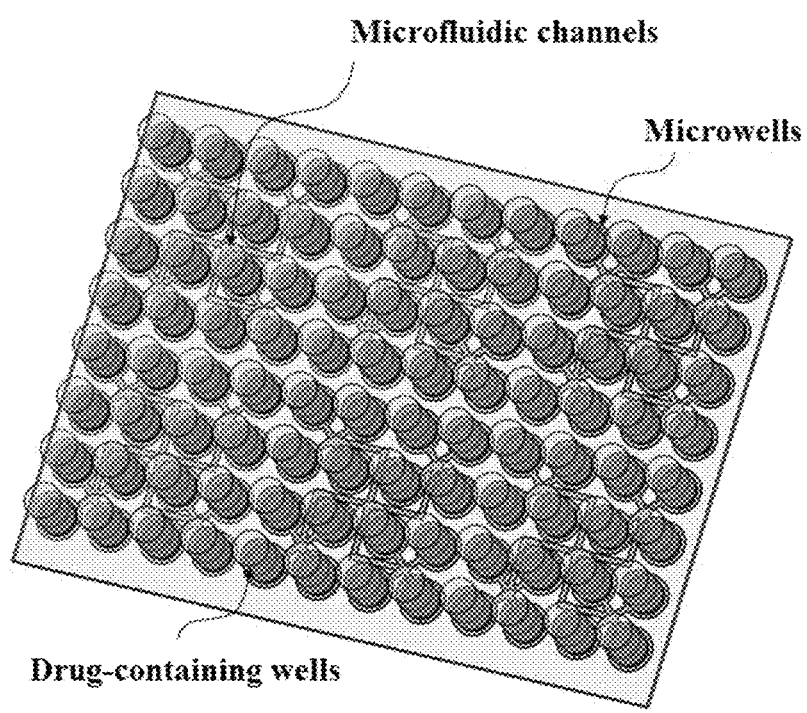
FIG. 14 shows an inverted state of an assembly of a microwell-based plate with microfluidic channels and a 96-well plate containing bioactive agents.

FIG. 14 shows an inverted state of the assembly of the microwell-based plate with microfluidic channels and the 96-well plate containing the bioactive agents.

Figure 15:
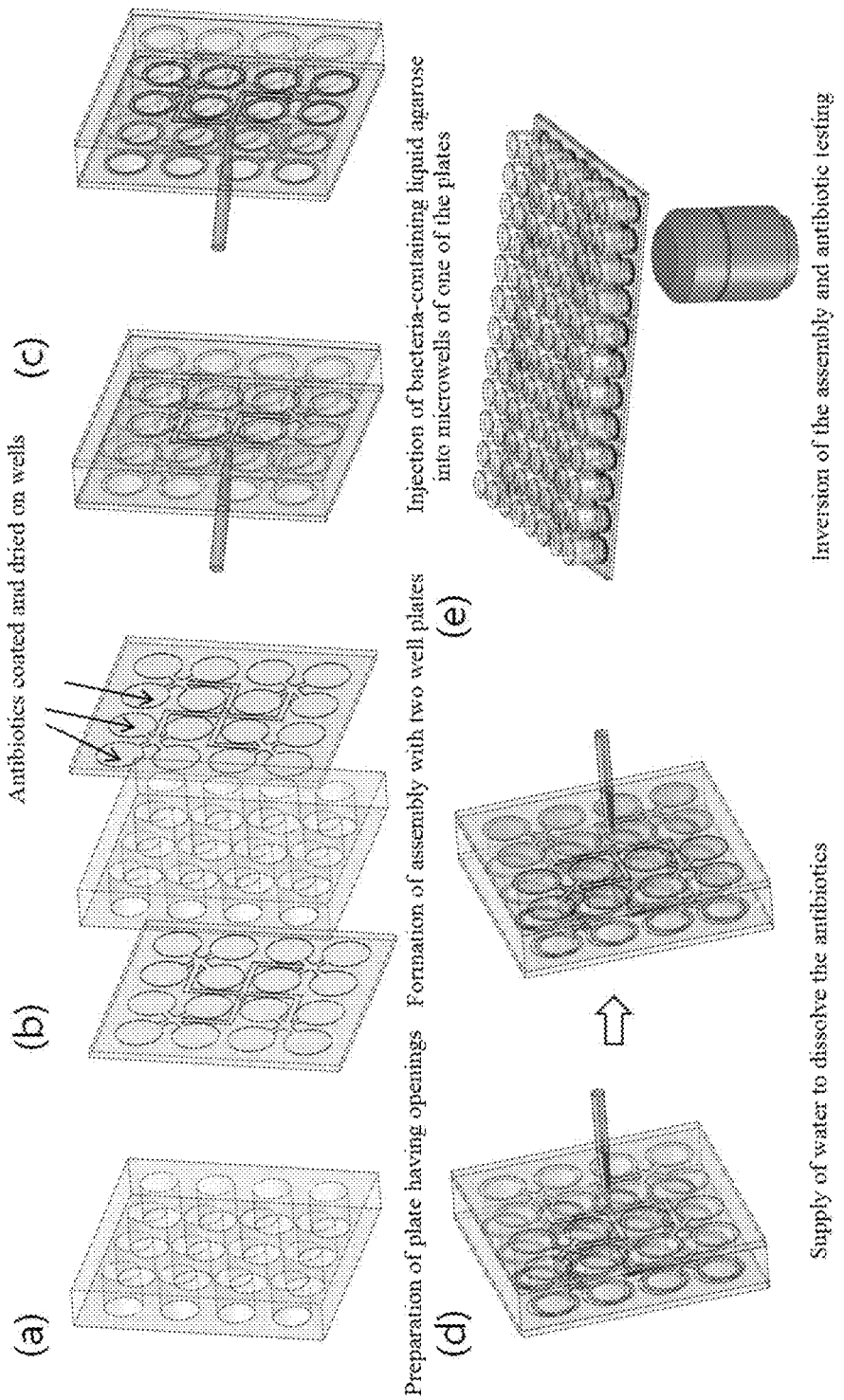
FIG. 15 shows a bioactivity testing process using a well plate system with microfluidic channels according to one embodiment of the present invention.

In one embodiment, there is provided a testing method using an assembly of two well plates having microfluidic channels and a well plate having a plurality of openings corresponding to the wells of the well plates having microfluidic channels. FIG. 15 shows a bioactivity testing process using a well plate system with microfluidic channels according to one embodiment of the present invention. Referring to FIG. 15, two well plates having microfluidic channels and a well plate having a plurality of openings corresponding to the wells of the well plates having microfluidic channels are prepared. Antibiotics are applied to the wells of one of the well plates having microfluidic channels and are dried. Next, the two well plates are coupled to the well plate having a plurality of openings to form an assembly. For assembly, all wells of the well plates having microfluidic channels correspond to the wells of the well plate having openings. Next, agarose with bacteria is injected through the microfluidic channels of one of the well plates having microfluidic channels and is gelled to form solid thin films. Next, water is supplied to spaces created by the formation of the assembly to dilute the dried antibiotics. As a result, the liquid antibiotics are filled in the spaces. The assembly is inverted to conduct bioactivity testing. The antibiotics in the form of solutions tend to lose their efficacy with the passage of time. When the antibiotics provided in the well plates are present in the form of dried drugs instead of in the form of liquids, as described above, they can be prevented from losing their efficacy with the passage of time. Solutions of the dried drugs in water can be directly used for susceptibility testing.

A third exemplary embodiment of the testing device according to the present invention may be in the form of a plate. The testing device in the form of a plate refers to a plate having a thickness of a thin film formed by solidifying a liquid medium containing a gelling agent. No microbe may be immobilized or included in the testing device. If needed, the testing device in the form of a plate includes a coupled form of a solid thin film and a gelling device for forming the solid thin film. Such testing devices in the form of plates are collectively called "microplates."

According to one embodiment, a gelling device may be used to fabricate the testing device in the form of a microplate. The gelling device may include a plate mold for accommodating a solid thin film having a predetermined thickness (normally 500 µm to 1 mm) and a planar cover. The plate mold is inserted into the planar cover to form an internal space having a gap corresponding to the thickness of the solid thin film. The plate mold is assembled and dissembled with the cover. The use of the gelling device enables the fabrication of microplates having various dimensions.

According to one embodiment, there is provided a method for fabricating the testing device in the form of a microplate. First, a cover and a plate mold which can be assembled and dissembled with the cover are prepared. The cover and the plate mold are designed to form an assembly (i.e. a gelling device) having an internal space when coupled to each other. After injection of a liquid medium in a subsequent step, a solid thin film is formed in the internal space. A gap having a thickness of the thin film is created between the plate mold and the cover to allow the solid thin film to have a plate shape. Likewise, the internal space takes the form of a thin plate. Next, the cover and the plate mold are coupled to each other to form an assembly having at least one opening. The opening may be present at the upper side of the assembly to allow for the injection of a liquid medium therethrough. Next, a mixture solution of a gelling agent-containing liquid medium and a microbe is injected into the internal space through the opening. Subsequently, the mixture solution is solidified to form a solid thin film in which the microbe is immobilized. Finally, the plate mold having the solid thin film is separated from the assembly to obtain a microplate. The plate mold can serve as a gelling device to form and accommodate the solid thin film.

Figure 16:
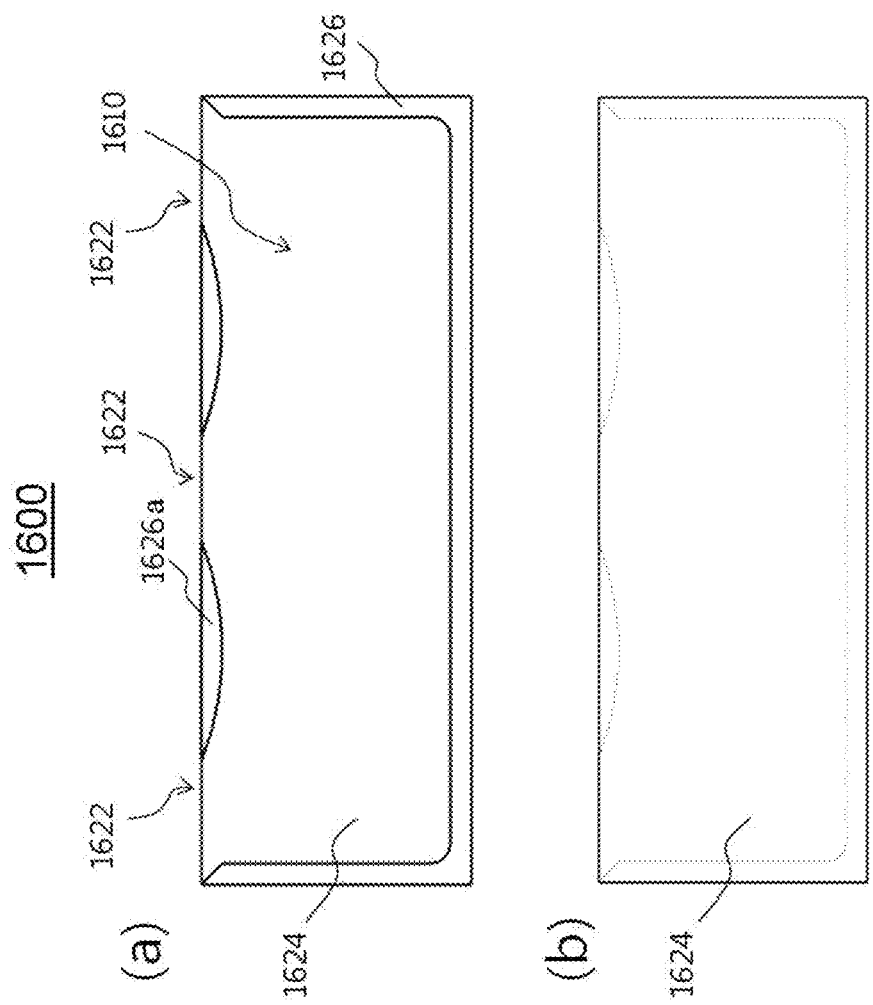
FIG. 16 shows a third exemplary embodiment of a testing device according to the present invention.

FIG. 16 shows the third exemplary embodiment of the testing device according to the present invention. In FIG. 16, (a) and (b) show front and rear sides of the testing device, respectively. Referring to FIG. 16, the testing device 1600 includes a solid thin film 1610 and a plate mold 1620 adapted to accommodate the solid thin film. The plate mold 1620 includes a plate 1624 and a frame 1626 to accommodate a liquid medium or the solid thin film. The plate 1624 may be made of a transparent or translucent material to allow for easy observation upon bioactivity testing using a microplate.

The plate mold 1620 corresponds to a gelling device for the fabrication of a microplate. The plate mold 1620 can be coupled to a cover to form an assembly, as described above. The internal space of the assembly has a plate-like shape due to the presence of the cover and the plate mold 1620. The frame 1626 is usually arranged along the periphery of the plate 1624. With this arrangement, the solid thin film 1610 has a particular shape, such as a rectangular shape. The frame 1626 has a thickness suitable to accommodate a liquid medium and allows the liquid medium to form the solid thin film 1610 having an appropriate thickness. After completion of the molding into the solid thin film 1610, the plate mold 1620 is separated from the cover. The frame 1626 ensures safe separation of the solid thin film 1610 accommodated in the plate mold 1620 from the assembly.

In the course of the fabrication of a microplate, a liquid medium is injected through at least one opening 1622 formed at the upper side of the assembly. Specifically, the opening 1622 may be formed at the upper side of the plate mold 1620 constituting the assembly. The opening 1622 may be provided in plurality at the upper side of the plate mold 1620. This facilitates injection of the raw material and prevents the occurrence of bubbles during injection.

The plate mold 1620 may further include humps 1626a. The opening 1622 may be defined by the humps 1626a. Similarly to the frame 1626, the humps can serve as spacers to stably maintain a proper interval when coupled to the cover in the subsequent stage. When the plate mold 1620 is separated from the cover after integration, the humps 1626 can play a role in supporting the solid thin film 1610 to safely accommodate the solid thin film 1610 in the plate mold 1620 and to separate the solid thin film 1610 from the cover while preventing the solid thin film 1610 from being pushed out of the plate mold 1620.

The microplate may have the same size as a general slide glass. The solid thin film has a thickness of 10 µm to 3 mm, preferably 100 µm to 1 mm, more preferably 500 µm to 1 mm. Grids may also be provided on the plate 1624 of the testing device 1600 to easily perceive the number of cells in the solid thin film 1610.

The cover having a predetermined shape is used to fabricate the testing device 1600 by molding, as described above. Depending on the shape of the cover, the testing device may be fabricated by an insertion- or slide-type molding process. The cover may be made of a transparent plastic material, such as polycarbonate, by a micromachining process.

Figure 17:
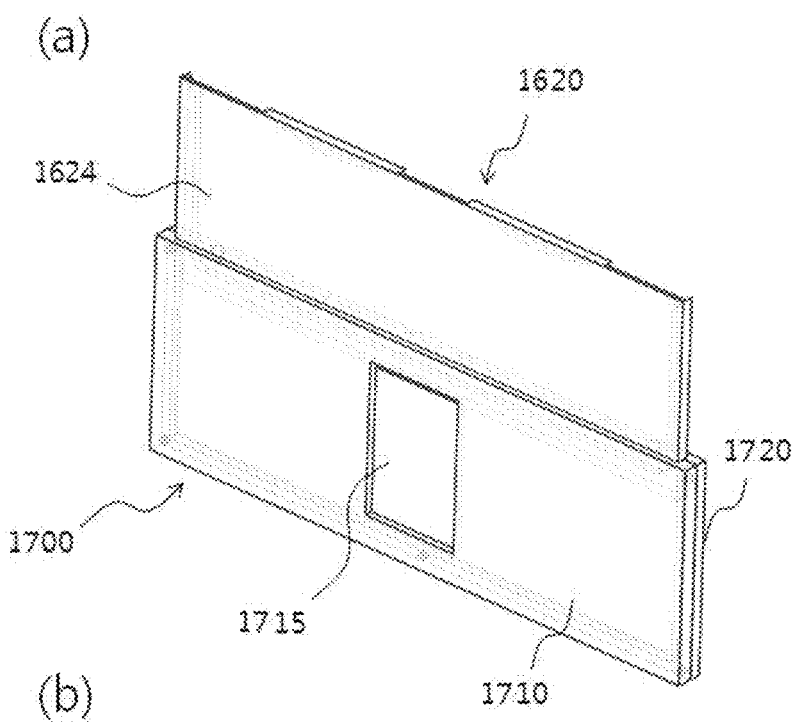
FIGS. 17 and 18 show the fabrications of testing devices using an insertion-type cover and a slide-type cover, respectively.
Figure 18:
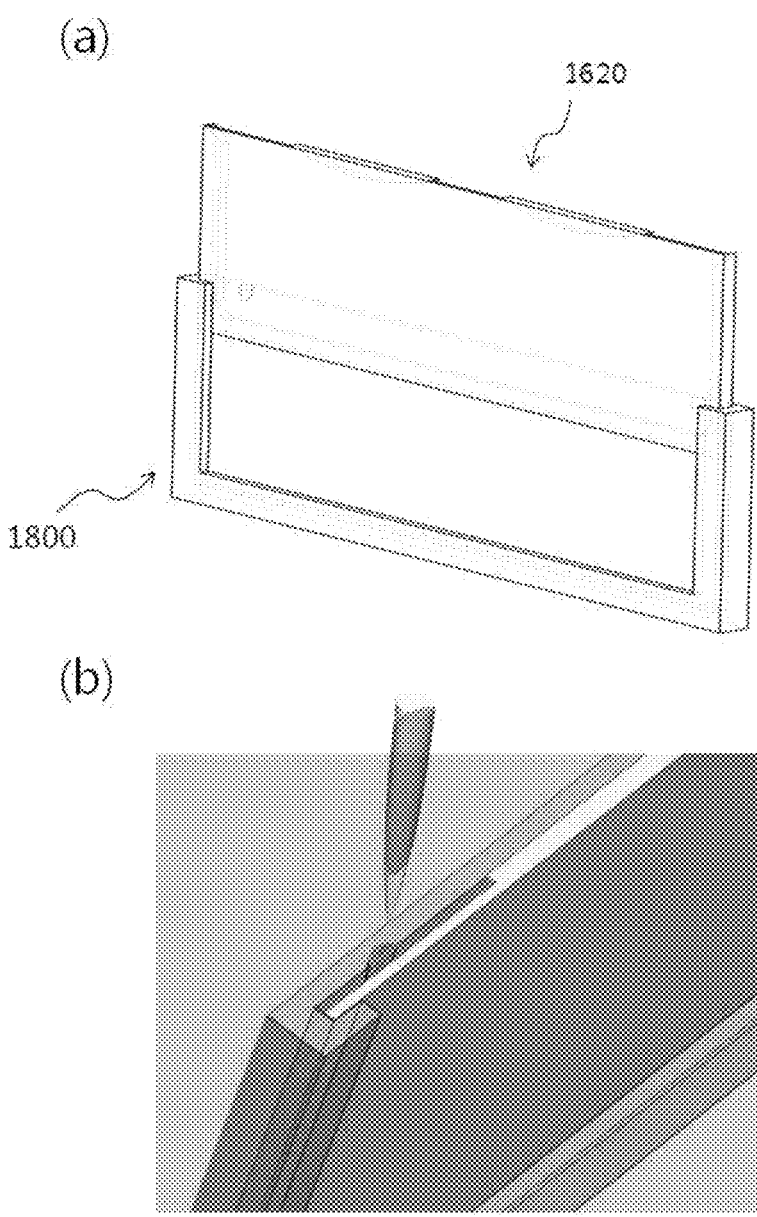

FIGS. 17 and 18 show the fabrication of testing devices using an insertion-type cover and a slide-type cover, respectively. In each of the figures, (a) shows the coupling mode of a cover and a plate mold, and (b) shows the injection of a liquid raw material through an opening formed at the upper side of an assembly of the cover and the plate mold.

In FIG. 17, the insertion-type cover 1700 may have a structure in which two plates, i.e. a first plate 1710 and a second plate 1720, are coupled to each other. The plate mold 1620 is inserted through an opening of the insertion-type cover 1700 to form an assembly. The assembly may have a plate-like shape in which all sides other than the opening are closed. After insertion, a liquid medium as a raw material for a solid thin film may be injected through the opening to fill an internal space between a plate 1624 of the plate mold 1620 and the second plate 1720 of the insertion-type cover 1700. After gelling of the raw material, a solid thin film is formed in the internal space. The plate mold 1620 is separated from the insertion-type cover 1700 to obtain a testing device. An opening 1715 may be formed at one side of the insertion-type cover 1700 to facilitate manual operation for separation of the plate mold 1620 inserted into the insertion-type cover 1700.

The slide-type cover 1800 of FIG. 18 may take the form of a plate mold whose one side is open. A process for molding a testing device using the slide-type cover 1800 of FIG. 18 is the same as that described in FIG. 17, except that one side of the cover 1800 is open.

Figure 19:
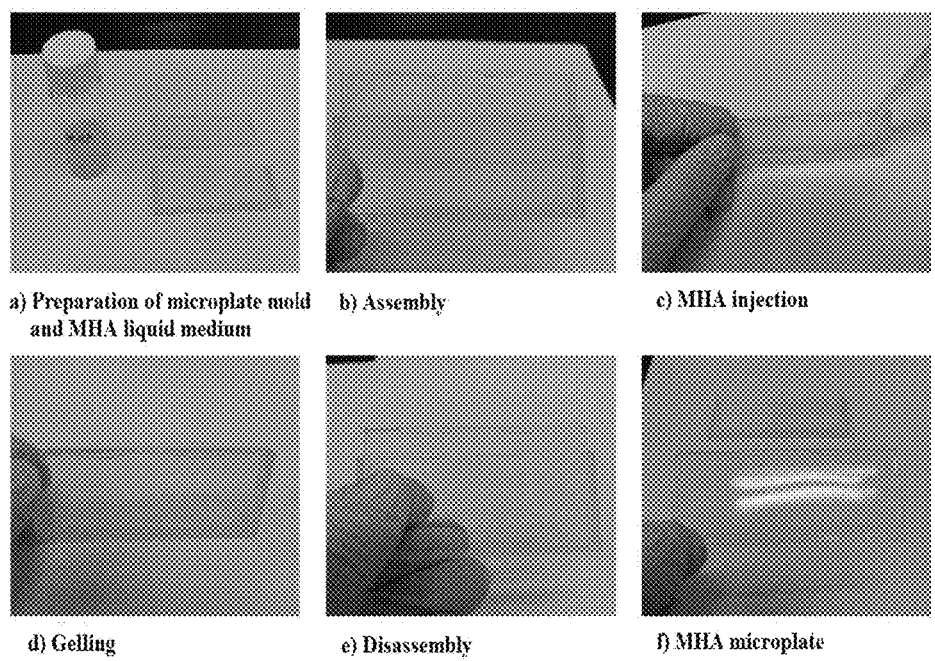
FIG. 19 shows the overall procedure of a process for producing a microplate.

FIG. 19 shows the overall procedure of a process for fabricating a microplate. In FIG. 19, a) shows a cover and liquid Mueller-Hinton Agar (MHA) for the fabrication of a microplate, b) shows assembly of the cover and a plate mold, c) shows injection of the MHA, d) shows gelling of the MHA, e) shows separation of the cover and the plate mold, and f) shows the final microplate.

According to one embodiment, there is provided a bioactivity testing method using a microplate fabricated by the above method. The testing method includes: providing a microplate having a solid thin film in which a microbe is immobilized; supplying a bioactive agent to the solid thin film and allowing the bioactive agent to diffuse into the solid thin film; and imaging the individual responses of the single microbial cells to the bioactive agent, and analyzing the images.

The use of the cell-immobilized solid thin film, which is formed by the solidification of a liquid medium due to a gelling agent, in the microplate enables tracking of single cell growth with the lapse of time, contributing to the investigation of cell differentiation. For example, the microplate may have a thickness of about 10 µm to about 1 mm and is interchangeable with a slide glass for a microscope. The use of the microplate ensures rapid absorption of the bioactive agent to the solid thin film by diffusion and enables tracking of single cell growth, thus facilitating the acquisition of information, such as minimum inhibitory concentration (MIC). The microplate can be used in various applications, for example, bacterial growth simulation under aerobic and anaerobic conditions, spore germination monitoring, and live/dead cell assay.

In one embodiment of the bioactivity testing method, diffusion effects of a bioactive agent can be observed by arranging a bioactive agent carrier, to which the bioactive agent is absorbed, on a microplate having a solid thin film in which cells to be observed are immobilized. The bioactive agent carrier may take the form of a hydrogel. The bioactive agent carrier may be produced by mixing the bioactive agent with a liquid oligomer, and curing the mixture solution by thermal curing or photocuring. In connection with the production method, Korean Patent No. 10-1101310, which was assigned to the same inventor of the present application, is hereby incorporated by reference.

In order to test various bioactive agents, various codes, such as graphical codes, color codes using superparamagnetism, or fluorescent codes, may be stamped into the bioactive agent-delivering particles to produce coded particles. For example, the particles may be coded by patterning based on a lithography process. As described above, a photocurable resin can be applied to the production of the bioactive agent-delivering particles, and an optical lithography process can be applied to the patterning of the bioactive agent-delivering particles. The bioactive agent-delivering particles may be patterned by various lithography processes known in the art, for example, optofluidic lithography, which is described in Korean Patent No. 10-1004769, and a combination of flow lithography and polymerization, which is described in U.S. Pat. No. 7,709,544. For example, codes may be formed on the particles by patterning labels representing '1' and '0' on the photocurable polymer. The labels are distinguished from each other depending on the degree of photocuring. For example, a digital micromirror device using no mask may be employed for optical lithography. In this case, various kinds of codes, for example, as many as one million kinds of codes, can be advantageously formed on the particles including the target substance. As an alternative example, magnetic nanoparticles may be used to form color codes on the particles. For example, a method for forming color codes using a magnetic ink is disclosed in Korean Patent Application No. 10-2010-0029613. According to this method, an external magnetic field is applied to a photocurable material including magnetic nanoparticles to align the magnetic nanoparticles in the photocurable material, and external light is applied to cure the photocurable material. In response to the intensity of the external magnetic field, the array of the magnetic nanoparticles is varied to emit different colors. By the application of such techniques, magnetic nanoparticles can be arranged so as to be distinguished from each other in one area of the particles, so that color codes can be formed on the particles. According to another example, fluorescent substances of different colors can be incorporated into the particles to code the particles.

As described above, a plurality of coded bioactive agent carriers having codes distinguishable from each other by the kind of the bioactive agents can be prepared. According to one embodiment, the use of the coded bioactive agent carriers enables multiplexing assay on a testing device, such as a microplate. The multiplexing assay may include the following stages. First, a plurality of coded bioactive agent carriers is prepared. The coded bioactive agent carriers contain bioactive agents and have codes distinguishable from each other by the kind of the bioactive agents. Next, the plurality of coded bioactive agent carriers is provided on a testing device including a microbe-containing solid thin film. Subsequently, the codes of the bioactive agent carriers arranged at particular locations of the testing device are read. Next, the individual changes of the microbe present at the particular locations caused by the diffusion of the bioactive agents are measured. The codes may be selected from the group consisting of graphical codes, color codes, and fluorescent codes.

Figure 21:
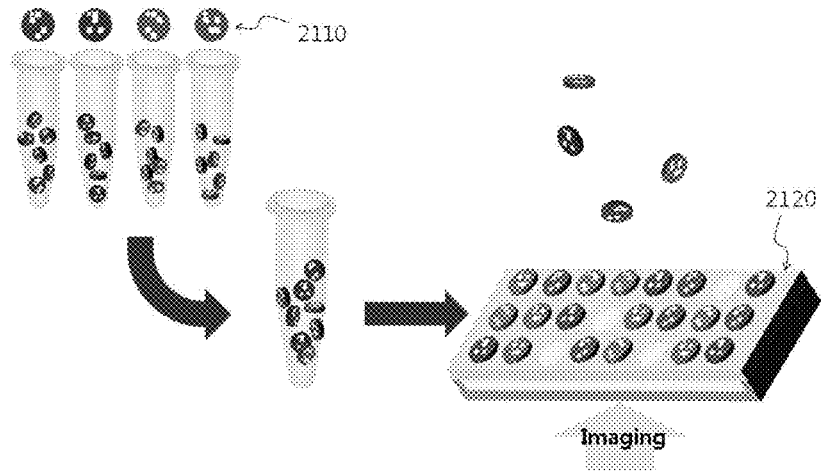
FIG. 21 schematically shows a multiplexing assay process on a microplate.

FIG. 20 shows coded microparticles as coded bioactive agent carriers for multiplexing assay according to one embodiment of the present invention. In FIG. 20, (a) shows coded microparticles containing various kinds and concentrations of bioactive agents, and (b) is an actual image of graphically coded hydrogel microparticles produced by curing a liquid photocurable oligomer. FIG. 21 schematically shows a multiplexing assay process on a microplate. By the use of coded particles 2110, five to ten hundred bioactive agents can be tested on a single microplate 2120.

In one embodiment, there is provided a testing system for multiplexing assay that uses coded particles and a testing device. The testing system for multiplexing assay includes: a thin film-like testing device fabricated by solidifying a mixture of gelling agent-containing liquid medium and a microbe; coded bioactive agent carriers for supplying bioactive agents to the testing device; a stage for supporting and observing the testing material; and an analyzing system for reading the codes of the bioactive agent carriers according to the location information of the testing device and observing the individual changes of the microbe caused by the delivery of the bioactive agents diffused from the coded bioactive agent carriers.

In one embodiment, the testing device may include wells for accommodating the bioactive agent carriers.

Figure 22:
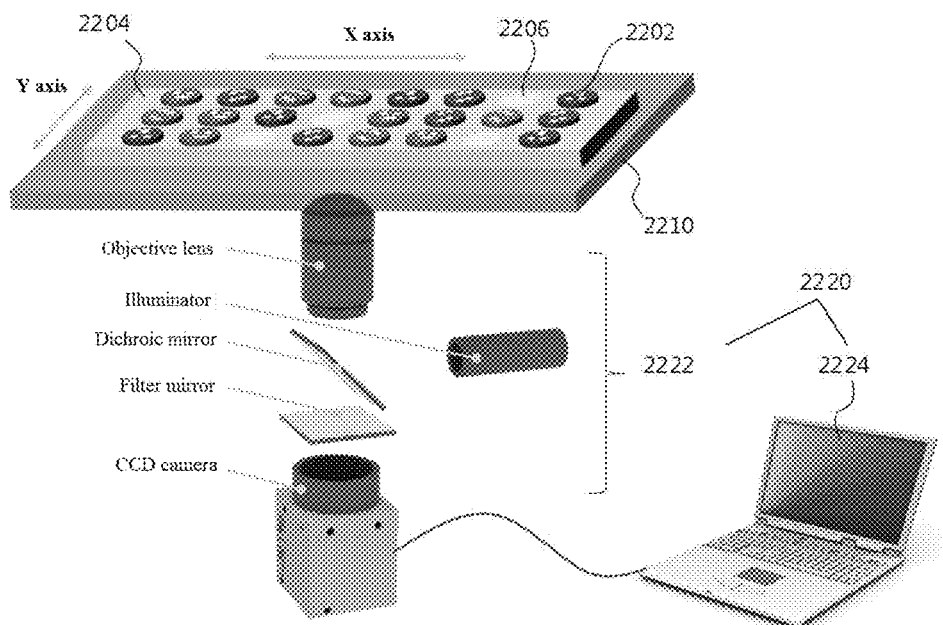
FIG. 22 shows one embodiment of a testing system for multiplexing assay.

FIG. 22 shows one embodiment of the testing system for multiplexing assay. The testing system for multiplexing assay includes coded particles 2202 containing bioactive agents, a testing device 2204, a stage 2210, and an optical measurement system 2220. The coded particles 2202 can be introduced into wells 2206 and aligned on the testing device 2204. By discriminating the codes of the coded particles 2202 through the optical measurement system 2220, changes of a microbe can be observed depending on the kind and concentration of the bioactive agents.

The optical measurement system 2220 includes an imaging system 2222 adapted to obtain images from targets and an image processing unit 2224 adapted to process and analyze the obtained images. The stage 2210 supports the testing device 2204 and can move the testing device 2204 in the width, length and height directions to observe the targets at desired locations. For full automation, the stage 2210 is preferably driven by means of a motor. The imaging system 2222 of the optical measurement system 2220 may include an objective lens, a mirror, an illuminator, and an element for imaging objects, such as a CCD or CMOS camera. For ease of statistical processing, the image processing unit 2224 processes raw images, acquires useful data from the processed images, and analyzes the data. When the testing system is used, multiplexing assay results can be obtained through real-time imaging within a few hours.

The testing system can be combined with coded drug carriers (coded microparticles having a diameter of 50 to 500 μm) to rapidly analyze several hundred kinds of drugs simultaneously, thus being very suitable for use in multiplexing assay drug screening or antibiotic susceptibility testing.

In the present invention, the rapid antibiotic susceptibility test (RAST) system innovatively reduces AST assay time for MIC determination by single bacterial time-lapse imaging. The RAST system immobilizes bacterial cells by using agarose so that single cell growth is able to be tracked under image systems such as microscopes and cell analyzers. Time-lapse images of single bacterial cells under different antibiotic culture conditions are automatically analysed by image processing to determine MIC. In the Examples section that follows, several standard bacteria of the Clinical and Laboratory Standard Institute (CLSI) were tested with several kinds of antibiotics. Well matched MIC values to those of CLSI were obtained only in 3-4 hours. The RAST system is expected to offer more efficient and proper medication in clinical area.

The present invention will be explained in more detail with reference to the following examples. However, these examples are not intended to limit the spirit of the invention.

EXAMPLES

1. Microfluidic Channels

Formation of Microfluidic Channels

Radial microfluidic channels with six branches were formed using soft-lithography. First, SU8 mold (2015 SU8, Microchem) was fabricated by employing photolithography. Polydimethylsiloxane (PDMS, Dow Corning) was mixed with a curing agent (10:1, w/w) and poured into the SU8. After baking at 150° C. for 10 min, the PDMS was peeled off and attached to the PDMS-coated slide glass by $O_2$ plasma treatment to obtain a radial microfluidic channel chip capable of testing antibiotics having five concentrations and a control with no antibiotic. There were six main channels that carried one side-branched channel each. Each of the main channels had a width of 500 μm and the side-branched channel had a width of 200 μm. Each of the channels had a thickness of 30 μm. A mixture of agarose and bacteria was allowed to flow in the main channels, and the bioactive agents were allowed to flow in the respective side-branched channels. In the middle of each main channel, there were anchors in the form of micro-sized posts for forming an interface between the agarose and each of the bioactive agents. The posts blocked the agarose from flowing into the side-branched channel. The sizes of the posts and the pitches between the posts were determined by mathematical calculations. For appropriate hydrophobicity to occur in the channel, the channel was prepared one day before experiment to increase the surface tension after $O_2$ plasma treatment.

Bacterial Fixation and Tracking of Bacterial Cell Growth

Agarose (UltraPure agarose, Invitrogen) was injected into the microfluidic channels to diffuse the antibiotics and to immobilize the bacteria. Agarose is a non-cytotoxic and biocompatible gelling agent, which is widely used for bacterial and fungal culturing. Agarose is a porous material that is generally used for DNA separation. Thus, most chemicals including macromolecules (DNA and proteins) and antibiotics can be freely diffused through an agarose matrix.

Agarose is solidified at a temperature lower than 36° C. The cultured bacteria were mixed with 2% agarose (1:3, v/v) at 45° C. and immediately injected into the microfluidic channels. The agarose-bacteria mixture was solidified at 25° C. for 1 min. The obtained microfluidic agarose channel (MAC) chip was placed on a hot plate and incubated at 37° C. To provide nutrients, liquid CAMHB medium was supplied through the side-branched channels. The growth of the bacteria was monitored using a microscope. Bacterial growth was not inhibited and could be clearly monitored in the MAC system.

Figure 23:
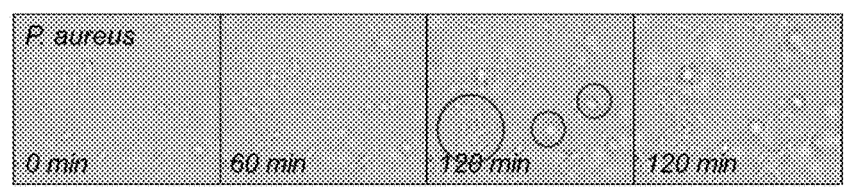
FIG. 23 shows bacterial immobilization and tracking of bacterial growth in a microfluidic agarose channel (MAC) system.

FIG. 23 shows bacterial immobilization and tracking of bacterial growth in the microfluidic agarose channel (MAC) system. Referring to FIG. 23, time-lapse microscopy images could be obtained to monitor the bacterial growth during observation. As a result of the observation, two types of bacterial growth were found, i.e. dichotomic cell type (large circle) and aggregative type (small circles). It is speculated that the aggregative type could be classified as a type of biofilm formation.

Image Processing

Figure 24:
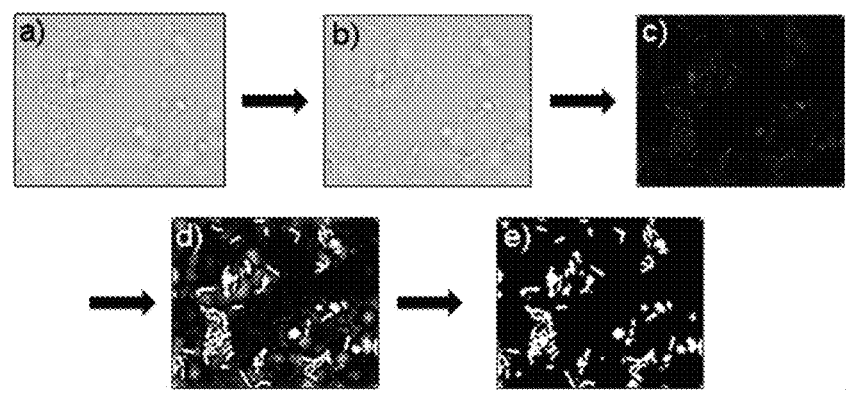
FIG. 24 shows image processing using an image processing program.

Bacterial cell images were taken with a CCD camera; the images were then processed to determine the MIC values of the antibiotics. The image data were transformed into digital data using an image processing program, which is coded in Matlab. For the calculations, RGB images were transformed into grey formatted images. The background data were eliminated to obtain sharp data without noise. Then, the contrast was enhanced to change the processed images into binary format images. FIG. 24 shows image processing using the image processing program. In FIG. 24, a) shows RGB images, b) shows transformation into grey format images, c) and d) show background elimination and optimization, respectively, and e) shows change of the processed images into binary format images to enhance the image contrast.

The Matlab program calculated the areas that were occupied by each bacterium. A longer incubation time allowed each bacterium to grow and occupy more area. The occupied areas were measured using the image processing program.

When the bacterial cells grew in the agarose, they did so by the two types of cell growth as shown in FIG. 23. The imaging processing program worked well for both types of growth, because it measured the sizes of the regions that the bacteria occupied. The dichotomic dividing type is well known and normal, but the aggregative type has not been reported thus far for in vitro culture systems. The MAC system of the present invention will assist in the research on the aggregative cell type (biofilms).

Antibiotic Susceptibility Testing in Microfluidic Agarose Channel System

200 μl of Mueller-Hinton agar including $5 \times 10^8$ cells/ml bacterial cells and 600 μl of 2% liquid agarose at 45° C. was mixed thoroughly by a vortex generator (vortex Genie 2). The agarose-bacteria mixture was placed in the main channels of the microfluidic channel system using a syringe pump (KdScientific) at stable flow rate (2 ml/hr) to prevent bursting into the side-branched channels. After the liquid agarose was solidified at room temperature to immobilize the bacteria in the main channels, the MHA medium containing the antibiotic was injected into the side-branched channels using the syringe pump at a rate of 10 μl/hr to diffuse into the agarose-bacteria mixture. Bacterial growth was monitored by using a microscope (40×) and a CCD camera. Images of bacterial growth were taken every hour and were analyzed by using the image processing program.

To validate the rapid antibiotic susceptibility test (RAST) system in the microfluidic agarose channel (MAC), general experimental bacteria (*Escherichia coli* DH5α and *Bacillus subtilis* ATCC 6633) and three standard bacteria (*Escherichia coli* ATCC 25922, *Staphylococcus aureus* ATCC 29213 and *Pseudomonas aeruginosa* ATCC 27853) of the Clinical and Laboratory Standard Institute (CLSI) were tested to determine the MIC values of amikacin, norfloxacin, tetracycline, and gentamicin.

In all cases, the MIC values were determined with small amounts of the antibiotics, media and bacteria (30,000 cells/one assay) within 2-4 hours. The obtained MIC values were verified by the conventional method (microdilution method) and compared with the MIC data of the CLSI.

In Table 1, the MIC values of the three antibiotics determined by the RAST method on the three standard CLSI strains are compared with those of CLSI (unit: μg/ml).

immobilized in an about 30 μm thick agarose matrix, different concentrations of antibiotics are diffused, and the bacterial single cell growth is tracked by microscopy according to the incubation time. Thereafter, the growth images are processed using an image processing program to determine MIC values. The entire AST process takes 3-4 hr, and thus the MAC system is rapid and produces data that is comparable in accuracy to the conventional AST results of the CLSI.

Figure 26:
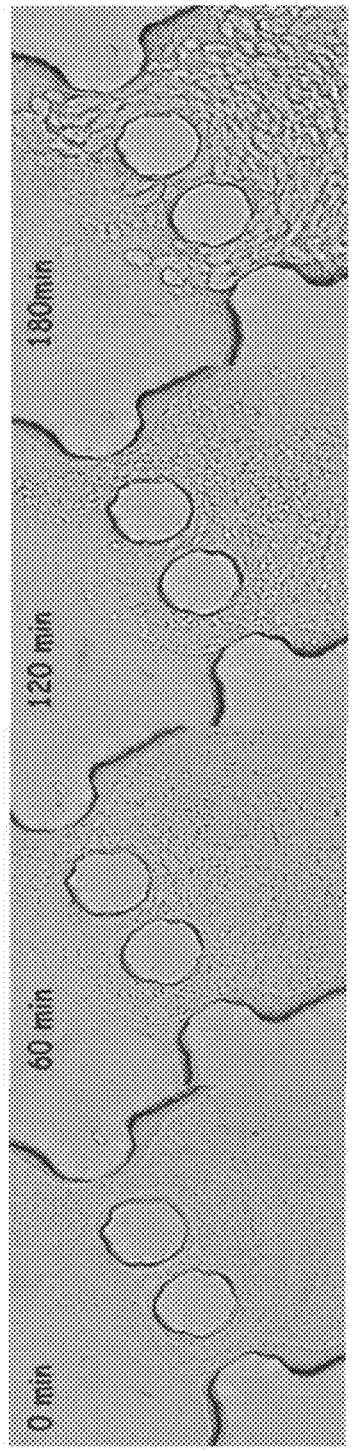
FIG. 26 shows time-lapse microscopy images showing the formation of a biofilm from single cells.

The time-lapse enlarged microscopy images of FIG. 26 shows the formation of a biofilm from single cells at the interface between the main channel and the side-branched channel of the MAC system of FIG. 3. As can be seen from FIG. 26, the biofilm was formed after aging for only 3 hr.

Figure 27:
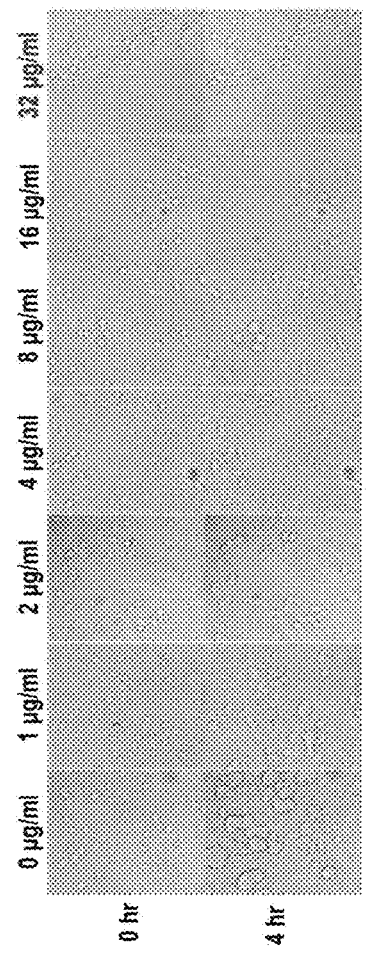
FIG. 27 shows changes of biofilms in a MAC system at different concentrations of an antibiotic.

FIG. 27 shows changes of biofilms in the MAC system at different concentrations of norfloxacin as an antibiotic. Referring to FIG. 27, as a result of susceptibility testing on the antibiotic against *P. aeruginosa* ATCC 27853, the MIC value was increased to a level of 32 μg/ml after biofilm formation by 4 hr aging in the MAC system. For reference, the CLSI MIC value against *P. aeruginosa* ATCC 27853 was in the range of 1-4 μg/ml.

Figure 28:
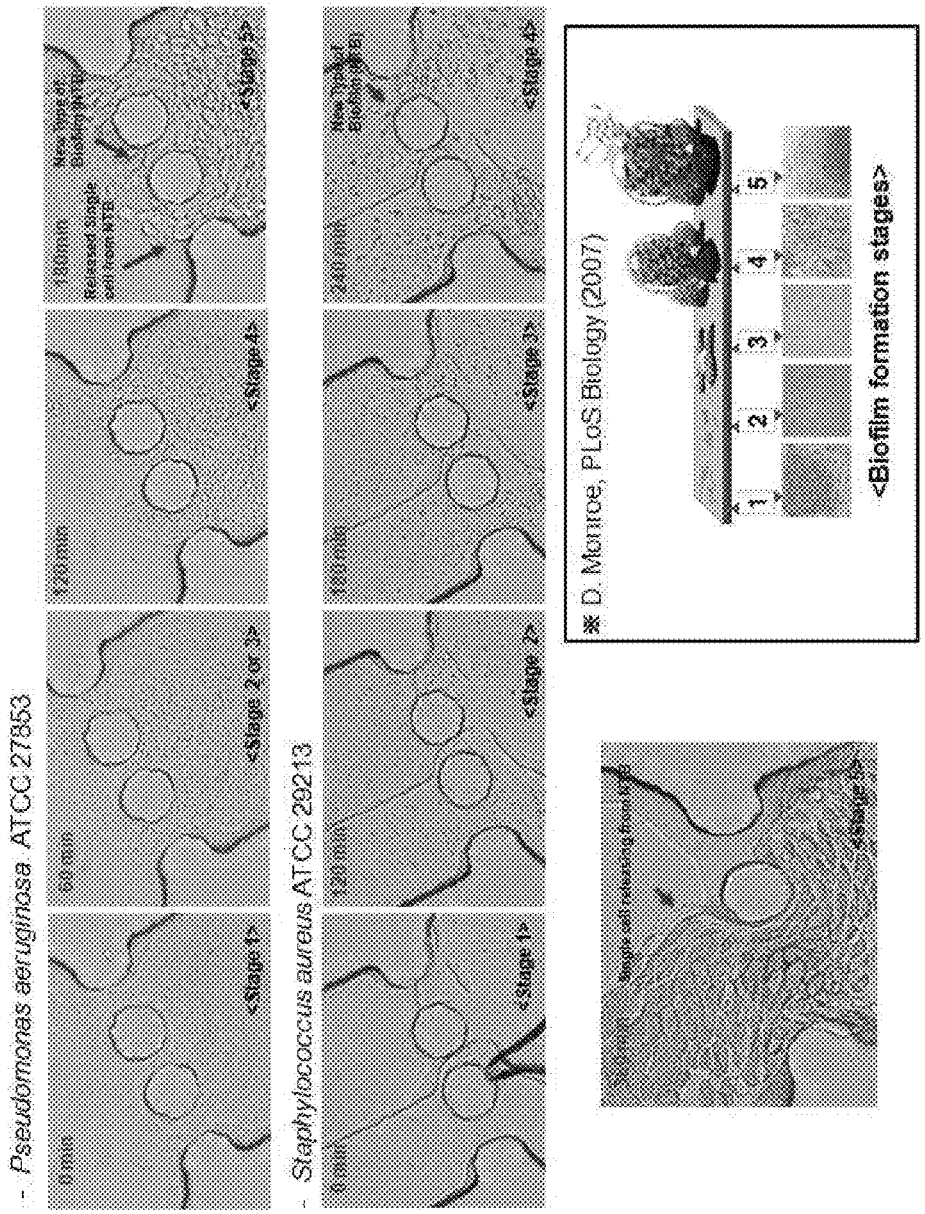
FIG. 28 shows time-lapse bright field images showing biofilm formation stages from two kinds of strains.

The time-lapse bright field images of FIG. 28 show biofilm formation stages from two kinds of strains. The images in the lower box of FIG. 28 show schematic dia-

TABLE 1

| Antibiotics | E. coli ATCC 25922 | | S. aureus ATCC 29213 | | P. aeruginosa ATCC 27853 | |
|---|---|---|---|---|---|---|
| | CLSI | RAST (Time*) | CLSI | RAST (Time) | CLSI | RAST (Time) |
| Amikacin | 0.5-4 | 4 (3 hr) | 1-4 | 4 (3 hr) | 1-4 | 4 (3 hr) |
| Norfloxacin | 0.03-0.12 | 0.03 (4 hr) | 0.5-2 | 0.5 (7 hr) | 1-4 | 2 (3 hr) |
| Tetracycline | 0.5-2 | 1 (3 hr) | 0.12-1 | 0.5 (3 hr) | 8-32 | 32 (3 hr) |
| Gentamycin | 0.25-1 | 1 (4 hr) | 0.12-1 | 1 (3 hr) | 0.5-2 | 2 (4 hr) |

*Time: Time required to determine the MIC (hours)

In conclusion, the present system greatly reduced the time for MIC determination and the quantities of the media, antibiotics and bacterial cells, and showed substantially the same MIC results when compared to conventional systems.

Figure 25:
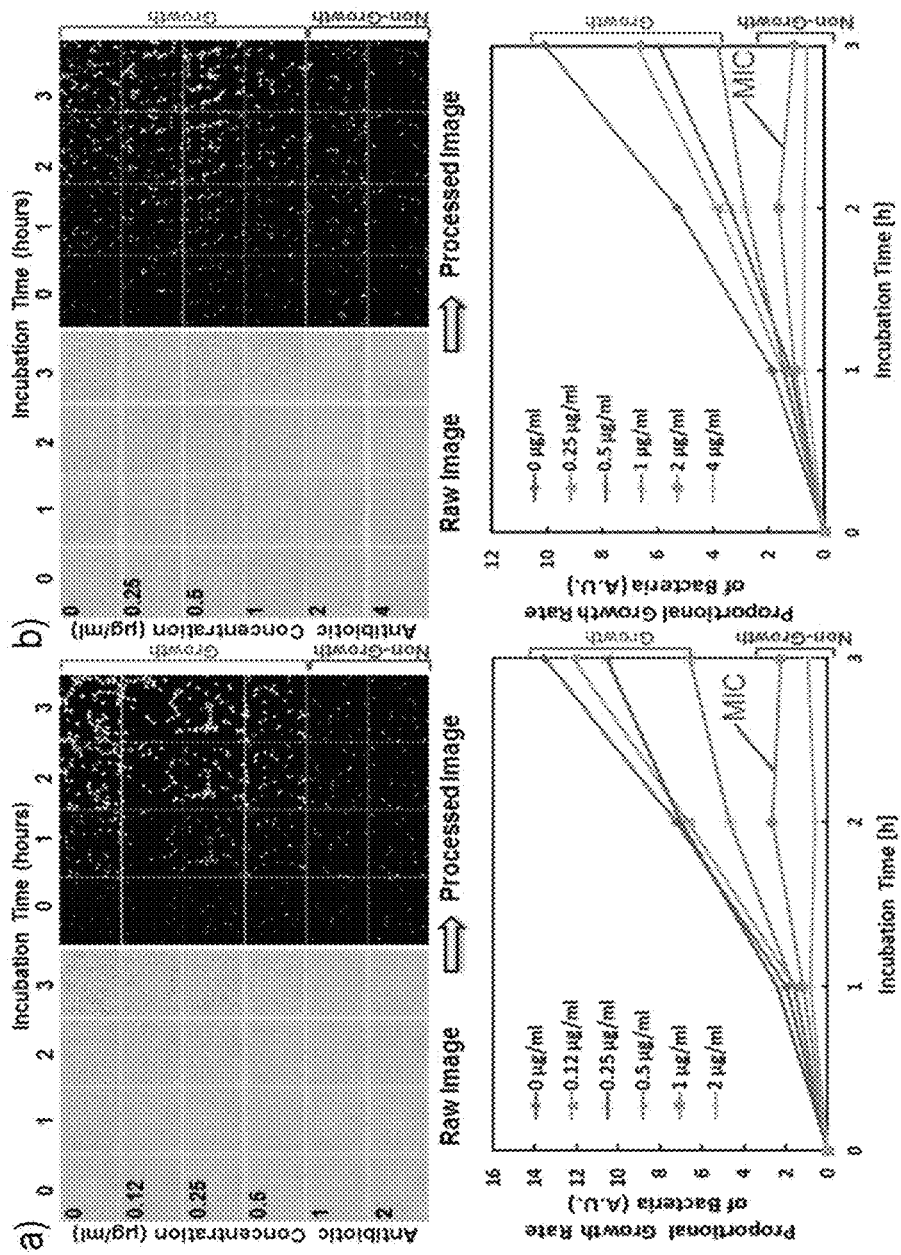
FIG. 25 shows MIC determination results obtained through image processing.

FIG. 25 shows MIC determination results obtained through image processing. In FIG. 25, a) shows the MIC determination of gentamicin against *S. aureus* ATCC 29213. The images of the left group are RGB images before processing, and the images of the right group are images after processing for clear observation. After image processing, the bacteria that occupied the area were measured and plotted on the graph for different concentrations of gentamicin according to the incubation time. The 1 μg/ml and 2 μg/ml concentrations did not permit bacterial growth. From these results, the MIC of gentamicin against *S. aureus* ATCC 29213 was determined to be 1 μg/ml. b) in FIG. 25 shows the MIC determination of gentamicin against *P. aeruginosa* ATCC 27853. In the same procedure as that stated above, the MIC of gentamicin against *P. aeruginosa* ATCC 27853 was determined to be 2 μg/ml. The MIC values were in the MIC ranges of the CLSI data.

The microfluidic channel system, such as MAC, provided in the present invention can innovatively reduce the analysis time and can reduce the quantities of the antibiotics, culture media and bacterial cells necessary for the analysis. The MAC system of the present invention can be considered the most rapid and accurate system among presently known AST systems. In the MAC system, solidified agarose is introduced into the microfluidic channels, bacteria are grams of a total of five biofilm formation stages described in the literature and microscopy images corresponding to the stages. Referring to FIG. 28, it can be very clearly observed that the single cells of *Pseudomonas aeruginosa* ATCC 27853 and *Staphylococcus aureus* ATCC 29213 strains formed respective biofilm colonies. Particularly, FIG. 28 clearly shows the fifth stage in which the single cells are released from the biofilm, which has been very difficult to observe in conventional systems. A new type of cell growth morphology was found in the MAC system and such new types of biofilms (NTBs) have not been reported thus far. The NTB formation appears to result from stress applied to the bacterial cells during immobilization by agarose.

As described above, the use of the MAC system allows for rapid observation of biofilm formation. In addition, biofilm formation can be directly and easily observed by optical microscopy and MIC or MBEC can be measured in a simple manner. Advantageously, the MAC system can be reduced in size and enables multiplexing assay. The MAC system clearly shows biofilm formation stages and can represent in vivo bacterial infection and biofilm formation. Hence, the MAC system is considered a very good tool for biofilm assay.

2. Microplates

Bacteria Preparation

*E. coli* and *B. subtilis* strains were allowed to grow in a 10 nm Mueller-Hilton (MH) broth overnight at an optimum temperature (*E. coli:* 37° C., *B. subtilis:* 30° C.). Next, 100 μl of the incubated cell broth was inoculated into 10 ml of a fresh MH broth and cultured for 5-6 hr until the optical density (OD) reached 0.5-0.6.

Fabrication of Microplates

Agar plates corresponding to a slide glass size (76 mm×26 mm×1 mm) were fabricated by the following procedure. First, a plate mold was inserted into a cover for microplate fabrication, and liquid Mueller-Hilton Agar (MHA) was fed into a space between the plate mold and the cover. After standing for 1 min, the MHA was solidified. The cover was removed to obtain a 1 mm thick agar plate.

For susceptibility testing on bacteria, a medium containing the bacteria was mixed with liquid MHA, and then the mixture was injected into a cover for microplate fabrication to obtain a bacteria-containing agar plate.

Production of Coded Particles

A liquid photocurable oligomer was selectively cured by UV light to obtain hydrogel microparticles. The photocurable oligomer included polyethylene glycol (700) diacrylate (PEG-DA) and 10 wt % of 2,2-dimethoxy-2-phenylacetophenone (UV initiator). Computer-controlled programmable two-dimensional spatial light modulators (SLMs) were used to produce particles having various graphical codes. The SLMs were controlled in the liquid oligomer to obtain particles into which various graphical codes were stamped. The particles had a diameter of 200 μm and a thickness of 50 μm. The remaining oligomer was removed by washing, and then the particles were post-cured to obtain fully cured hydrogel particles. The hydrogel particles were dried in desiccators for 6 hr and antibiotics were absorbed to the hydrogel microparticles over 12 hr. After completion of the antibiotic absorption, the particles were dried in desiccators for 12 hr.

For application to bioactivity testing, kanamycin or ampicillin was loaded onto the hydrogel microparticles. About 3.7 nl of the antibiotic solution was contained per particle and its weight was measured. The microparticle was found to contain 300 ng, 150 ng, 75 ng, 37.5 ng, 18.8 ng or 0 ng of ampicillin or 150 ng, 75 ng, 37.5 ng, 18.8 ng, 9.4 ng or 0 ng of kanamycin.

Test Examples

Imaging of Single Cells

The single cell growths of B. subtilis and E. coli were tracked on the microplates and images thereof could be obtained. About 1 μl of incubated cell broth was loaded onto the MHA microplates. Thereafter, the single cell growths were observed using a microscope (×400) at 0, 60, 120 and 180 min. The single cells of both B. subtilis and E. coli were tracked and binary fission growth thereof was confirmed.

Figure 29:
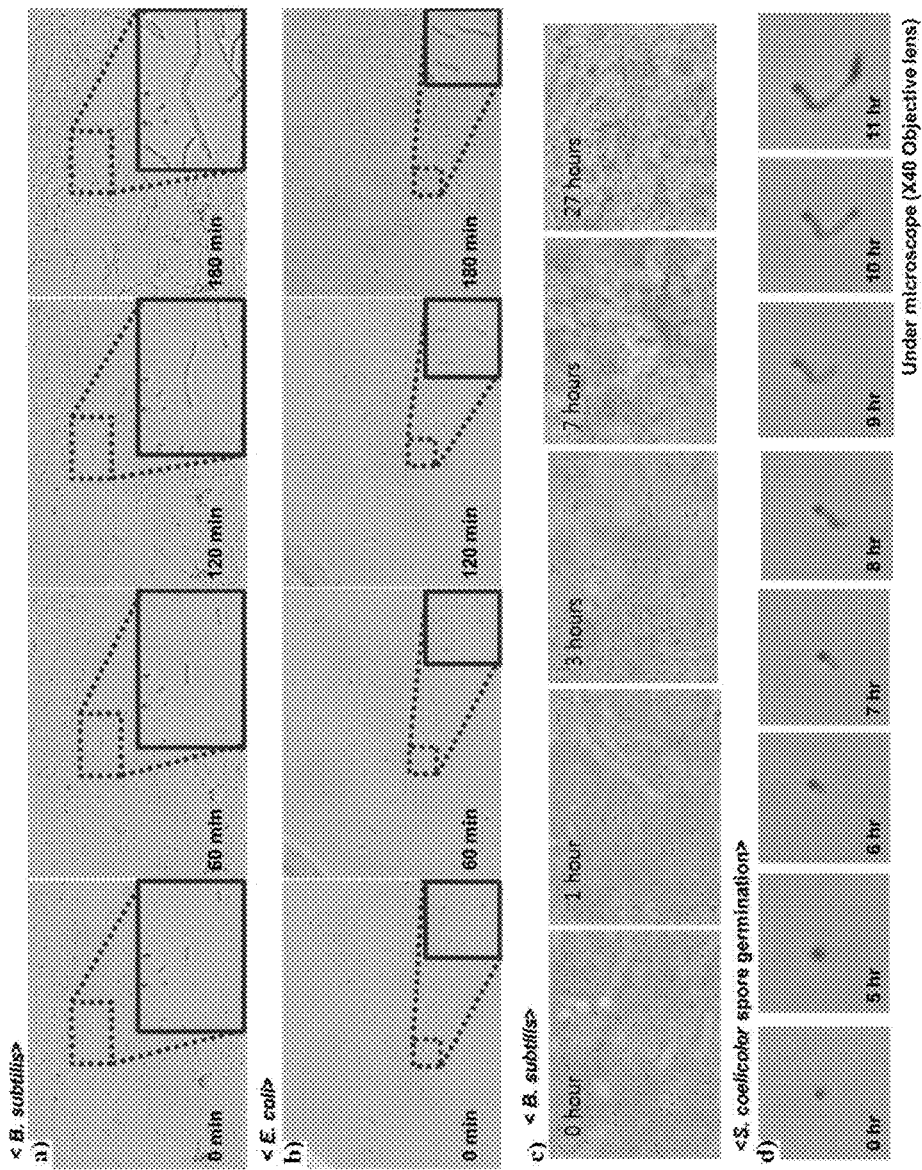
FIG. 29 shows time-lapse microscopy images showing changes in the growth of some microbes.

The time-lapse microscopy images of FIG. 29 show changes in the growth of some microbes. In FIG. 29, (a) and (b) show the single cell growths of B. subtilis and E. coli on the microplates, respectively, and (c) shows the single cell growth of B. subtilis in the microplate.

After the cells were mixed with MHA medium, they were allowed to grow under the surface of the microplate, i.e. under anaerobic conditions, and on the surface of the microplate, i.e. under aerobic conditions. That is, the microplate can be used to observe both anaerobic and aerobic bacteria during culture because it provides both anaerobic and aerobic conditions. Referring to (a) in FIG. 29, the single cell growth of B. subtilis loaded onto the microplate was observed, and as a result, the cells were found to have a rod-like structure (under aerobic conditions). Referring to (c) in FIG. 29, B. subtilis cells mixed with agar in LB medium were loaded into the microplate, the single cell growth thereof was observed, and as a result, the cells were found to have a filament-like structure (under anaerobic conditions). From these results, it can be seen that the microplate system can be used under both aerobic and anaerobic conditions, contributing to labor and equipment cost reduction. Furthermore, the microplate can be applied to cell differentiation studies under various conditions, such as oxidative stress, antibiotics, aerobic conditions, and anaerobic conditions.

2XYT medium for spore germination was diluted to 40 times, and a heat shock was applied thereto at 50° C. for 10 min. After pouring into ice, 1 μl of the spore solution was dropped onto the microplate and 3-5 μl of the MHA medium was overlaid to immobilize the spores. The immobilized spores were observed using a microscope.

The spore germination process of S. coelicolor was observed and images thereof are shown in (d) of FIG. 29. All images were taken under a microscope (×40 objective lens). Germination of the wild type spores was clearly observed. The spores began to geminate 6 hr after loading and their mycelia continuously extended for 11 hr until observation was finished. The germination profiles of two kinds of mutants (mshA and sigR-rsrA) through the microplate system were compared with those of their wild types. As a result, the germination of the mutant mshA was delayed for 1 hr compared to its wild type. Less germination was observed in the mutant sigR-rsrA than in its wild type. From the above results, it could be first found that the microplate can be used to track the germination of spores on solid media.

Single cell imaging using the microplate can contribute to in-depth research into bacterial morphology and physiology. The use of the microplate enables culture or long-time observation of bacterial cells, unlike conventional methods using thin agar pads. In addition, bacterial cells can be observed at a thickness as small as tens to hundreds of micrometers in the microplate, unlike in conventional agar plates. Therefore, the microplate can be used to track single cell growth. Another advantage of the microplate is that spore germination can be observed on solid media. As can be seen from the foregoing, the microplate has proven its applicability in various fields.

Antibiotic Susceptibility Testing

Microparticles containing ampicillin or kanamycin were loaded onto a microplate mixed with E. coli cells or B. subtilis cells. The microplate was fabricated by the above method. The growth of the cells around the microparticles was observed with the passage of time.

Figure 30:
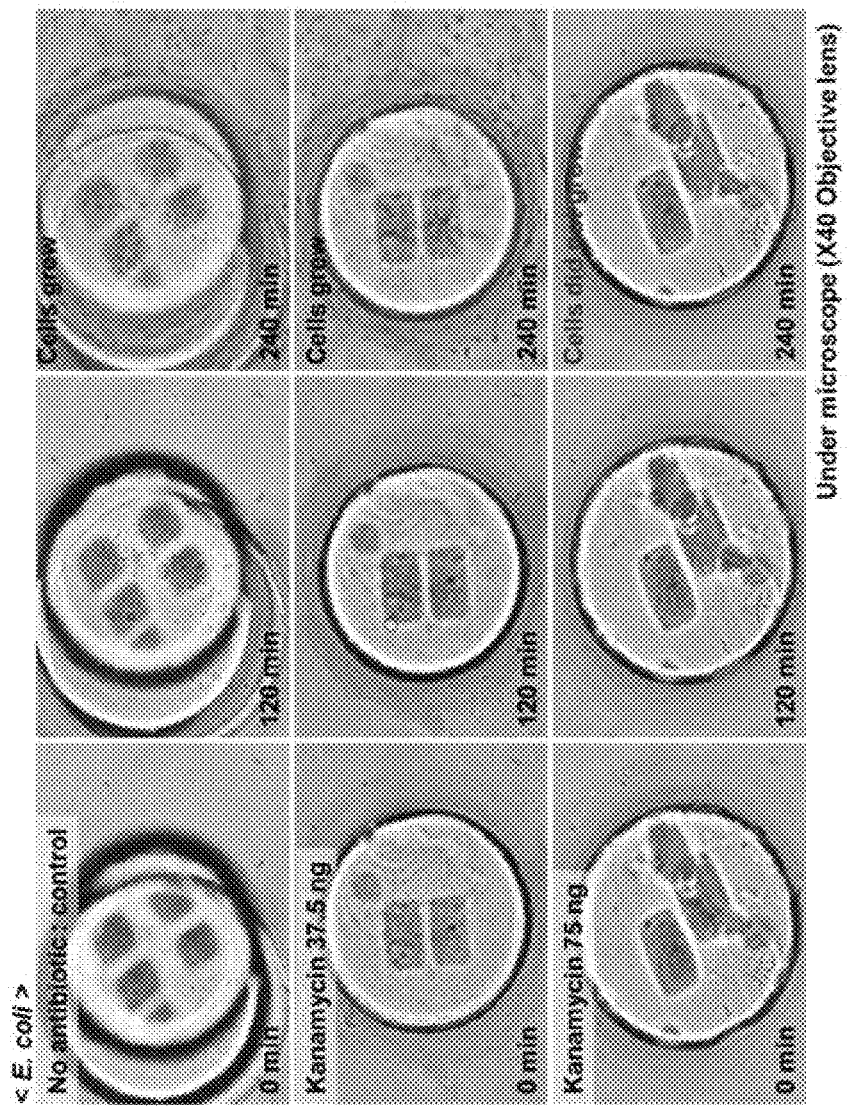
FIG. 30 shows time-dependent changes of *E. coli* cells as a function of the content of kanamycin in microparticles.

FIG. 30 shows time-dependent changes of the E. coli cells as a function of the content of kanamycin in the microparticles. Referring to FIG. 30, the bacterial growth was inhibited around the microparticles containing a large amount of the antibiotic (75 ng per microparticle) (exceeding the MIC). In contrast, the growth of the bacteria was observed in the microparticles containing no antibiotic or a small amount of the antibiotic (less than the MIC).

AST conducted using the microparticles on the microplate system is much more efficient than AST on agar plates. For comparison, disk diffusion AST (i.e. Kirby-Bauer test), a common method that is widely in use for AST, was conducted.

In the disk diffusion AST, filter disks containing an antibiotic were placed on an agar plate into which bacteria were inoculated. The susceptibility of the bacteria was confirmed by measuring the diameters of clear zones around the antibiotic filter disks after passage of 16-24 hr. For the susceptibility testing, about 20 ml of an agar medium plate per plate and about 10-100 µg of the antibiotic per filter disk were required. In the present test, only about 20 filter disks (each having a diameter of 6 mm) could be loaded onto one plate.

AST using the microplate system of the present invention has several advantages over the KB test. First, since 2.0 ml of an agar medium per microplate and 0.01-1 µg of an antibiotic per particle are required in the microplate system, the volume of the medium can be reduced to about one tenth to one hundredth when compared to that of a medium used in common AST. Second, doubling of bacteria under the antibiotic-containing particles can be tracked by time-lapse imaging of the microplate system. Third, hundreds of antibiotic-containing microparticles can be theoretically loaded onto one microplate. That is to say, when AST is conducted on hundreds of different kinds of antibiotics, the KB test requires 20-30 agar plates while the microplate-based test requires only one microplate.

The use of the testing device in the form of a microplate can reduce the analysis time, the endeavor of researchers, the amount of bioactive agents, the amount of media, and the size of plates, thus being advantageous in terms of economic efficiency.

Figure 31:
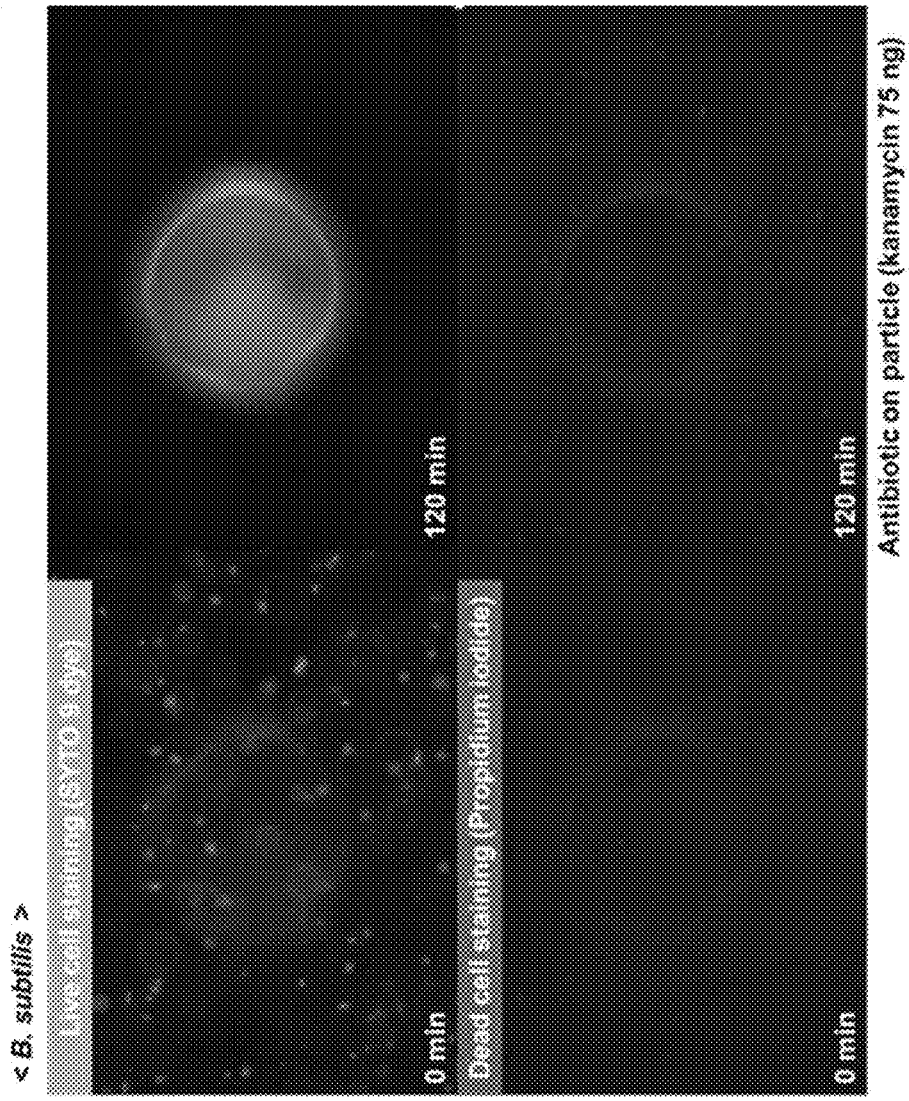
FIG. 31 shows results of live/dead cell assay performed on microplates.

In addition, the use of the microplate system enables live/dead cell assay on solid media to confirm whether cells are alive or dead after antibiotic treatment. LIVE/DEAD® BacLight™ Bacterial Viability Kit (Cat L7012, Invitrogen) can be used to perform live/dead cell assay. The commercial kit contains a green emitting phosphor (SYTO®9) for live cells and a red emitting phosphor (propidium iodide) for dead cells. Live/dead cell assay was performed by mixing *B. subtilis* bacteria with 1 ml of a solution of MHA and LIVE/DEAD® BacLight™ Bacterial Viability Kit to fabricate a microplate, and loading antibiotic-containing microparticles onto the microplate. Kanamycin was used as the antibiotic and 75 ng of kanamycin was contained per microparticle. FIG. 31 shows results of live/dead cell assay performed on microplates. Referring to FIG. 31, no color changes were observed when the particles with no antibiotic were used, whereas a decrease in the number of green spots and an increase in the number of red spots were observed 120 min after the antibiotic-containing microparticles were loaded. These results indicate that the bacteria were killed by the antibiotic released from the microparticles.

As demonstrated above, effective research on live/dead cells can be conducted using the microplate.

Although the present invention has been described with reference to the accompanying drawings and the foregoing embodiments, those skilled in the art will appreciate that various variations and modifications can be made to the embodiments without departing from the spirit and scope of the invention as disclosed in the appended claims.

What is claimed is:

1. A method for observing the responses of one or more microbial cells to a bioactive agent, comprising:
   providing a mixture solution of a gelling agent-containing liquid medium and one or more microbial cells;
   gelling the mixture solution to form a gelled matrix wherein the one or more microbial cells is immobilized inside the gelled matrix;
   providing a bioactive agent into the gelled matrix and allowing the bioactive agent to diffuse into the gelled matrix so that the bioactive agent is delivered to the one or more microbial cells;
   tracking at least one individual microbial cell directly among the one or more microbial cells by a microscopy and imaging an increase in an area occupied by growth of the at least one individual microbial cell with the lapse of time; and
   analyzing the time-lapse images.

2. The method according to claim 1, wherein a thickness of the gelled matrix is adjusted and/or optical focusing is performed for imaging the single microbial cells are observed.

3. The method according to claim 1, wherein the imaging is carried out to determine growth, division or aggregation of the one or more microbial cells.

4. The method according to claim 1, wherein the gelling agent is selected from the group consisting of agar, agarose, gelatin, alginate, collagen, fibrin, and mixtures thereof.

5. The method according to claim 1, wherein the gelled matrix is formed using a gelling device that has at least one receiving portion having an internal space where the mixture solution is retained.

6. The method according to claim 5, wherein the receiving portion comprises a microfluidic channel structure.

7. The method according to claim 6, wherein the microfluidic channel is hydrophilized.

8. The method according to claim 1, wherein the imaging step further comprises observing changes in the growth of the one or more microbial cells depending on a concentration of the diffused bioactive agent and the analyzing is carried out on the obtained images.

9. The method according to claim 8, wherein the imaging is carried out to observe a contact interface between the one or more microbial cells-immobilized in the gelled matrix and the bioactive agent, and the analysis is carried out on the obtained images.

10. The method according to claim 8, wherein a minimum inhibitory concentration (MIC) or a minimum biofilm eradication concentration (MBEC) of the bioactive agent is determined based on analysis of the images.

11. The method according to claim 8, wherein the bioactive agent susceptibility and resistance of the one or more microbial cells are determined based on analysis of the images.

12. The method according to claim 1, wherein the responses of the one or more microbial cells are analyzed by at least one of a number of one or more microbial cells, occupied area, and cell growth morphology of the one or more microbial cells in the images.

13. A method for observing the responses of one or more microbial cells to a bioactive agent, comprising:
   providing a bioactive agent into a microbe-immobilized solid thin film based on at least one gelling agent selected from the group consisting of agar, agarose, gelatin, alginate, collagen, and fibrin and allowing the bioactive agent to penetrate into the solid thin film by diffusion so that the bioactive agent is delivered to the one or more microbial cells; and
   tracking at least one individual microbial cell directly among the one or more microbial cells with an optical measurement system and imaging an increase in an area occupied by growth of the at least one individual microbial cell.

14. The method according to claim 13, wherein the solid thin film has a thickness of 1 µm to 5 mm.

15. The method according to claim 13, wherein the optical measurement system comprises an imaging system adapted to obtain images from targets and an image processing unit adapted to process and analyze the obtained images.

16. The method according to claim 13, wherein the changes in the growth of the one or more microbial cells are analyzed by calculating areas occupied by the one or more microbial cells in the images.

17. A method for observing the responses of one or more microbial cells to a bioactive agent, comprising:
- contacting a gelling agent-containing liquid medium with the one or more microbial cells;
- solidifying the gelling agent-containing liquid medium to form a gelled matrix in which the one or more microbial cells are immobilized by the gelled matrix;
- providing a bioactive agent into the gelled matrix and allowing the bioactive agent to diffuse into the gelled matrix so that the bioactive agent is delivered to the immobilized one or more microbial cells;
- incubating the immobilized one or more microbial cells for a certain time; and
- tracking at least one individual microbial cell directly among the one or more microbial cells by a microscopy and imaging an increase in an area occupied by growth of the at least one individual microbial cell.

18. The method according to claim 17, wherein the imaging step further comprises observing changes in growth of the microbe depending on a concentration of the diffused bioactive agent.

19. The method according to claim 17, wherein the responses of the microbe are analyzed by at least one of number, occupied area, and cell growth morphology of the one or more microbial cells in the images.

20. A method for an antibiotic susceptibility testing (AST), comprising:
- providing one or more microbial cells;
- providing a gelling agent capable of immobilizing the one or more microbial cells, wherein the gelling agent is selected from the group consisting of agar, agarose, gelatin, alginate, collagen, fibrin, and mixtures thereof;
- providing a bioactive agent capable of inhibiting growth of the one or more microbial cells;
- forming a solid thin film comprising the one or more microbial cells, the gelling agent, and the bioactive agent, wherein the one or more microbial cells are immobilized by the gelling agent;
- incubating the one or more microbial cells;
- tracking at least one individual microbial cell directly among the one or more microbial cells by a microscopy and imaging an increase in an area occupied by growth of the at least one individual microbial cell according to an incubation time and a concentration of the bioactive agent, wherein an image from the imaging step is taken as a microscopic picture from the microscopy;
- based on the image, determining a minimum inhibitory concentration (MIC) by analyzing the occupied area or a morphology based on the growth of the at least one individual microbial cell; and
- obtaining the result of the AST against the bioactive agent based on the step of determining the MIC.

21. A method for analyzing one or more microbial cells interacting with a bioactive agent, comprising:
- providing one or more microbial cells;
- providing a gelling agent capable of immobilizing the one or more microbial cells, wherein the gelling agent is selected from the group consisting of agar, agarose, gelatin, alginate, collagen, fibrin, and mixtures thereof;
- providing a bioactive agent capable of inhibiting growth of the one or more microbial cells;
- forming a solid thin film comprising the one or more microbial cells, the gelling agent, and the bioactive agent, wherein the one or more microbial cells are immobilized by the gelling agent;
- incubating the one or more microbial cells; and
- tracking at least one individual microbial cell directly among the one or more microbial cells by a microscopy and imaging an increase in an area occupied by growth of the at least one individual microbial cell.

* * * * *